United States Patent
Grimblatov

(10) Patent No.: US 6,261,236 B1
(45) Date of Patent: Jul. 17, 2001

(54) BIORESONANCE FEEDBACK METHOD AND APPARATUS

(76) Inventor: Valentin Grimblatov, 3000 Ocean Pkwy. #22, Brooklyn, NY (US) 11235

( * ) Notice: Subject to any disclaimer, the term of this patent is extended or adjusted under 35 U.S.C. 154(b) by 0 days.

(21) Appl. No.: 09/178,788

(22) Filed: Oct. 26, 1998

(51) Int. Cl.$^7$ ........................................................ A61B 5/02
(52) U.S. Cl. ............................................. 600/500; 600/479
(58) Field of Search ........................... 600/300, 481–486, 600/500–508, 476, 479; 128/900

(56) References Cited

U.S. PATENT DOCUMENTS 5,163,439 * 11/1992 Dardik ................................. 600/485
5,694,939 * 12/1997 Cowings ............................... 600/481

* cited by examiner

Primary Examiner—Cary O'Connor
Assistant Examiner—Michael Astorino
(74) Attorney, Agent, or Firm—I. Zborovsky

(57) ABSTRACT

A biofeedback method and apparatus for applying a physical action to a subject for treatment purposes and for other applications is disclosed. The method and apparatus disclosed include the steps of coordinating the physical action to systolic upstroke and diastolic drain cycles of subject's peripheral blood flow. Coordination to the cycles of blood flow synchronizes the treatment action with homoeostatic rhythms of the body, which along with automatic dose individualization substantially enhance efficiency and predictability of the treatment effect. The method and apparatus are also used for diagnostic purposes.

28 Claims, 18 Drawing Sheets

BIORESONANCE FEEDBACK METHOD AND APPARATUS

BACKGROUND OF THE INVENTION

The present invention relates to a method of and an apparatus for a biofeedback feedback for individual co-ordination of physical factors applied to a subject for treatment purposes among other applications with physiological parameters of the subject.

Continued metabolism is the common denominator of life. Biological systems require energy for continual metabolism, functioning and restoration. Normal cellular metabolism provides energy and homeostatic heat for nominal biological system function. The study of many biological objects proves that cellular metabolism and almost all homeostatic processes are oscillating, and the oscillations are determined by the state of system itself/Malik M., *Heart Rate Variability*, NY, 1995; Friedman H., Lubart R., Proc. SPIE, Vol.2630, pp.60–64, 1996/The oscillations are driven by complex of mechanisms having non-linear nature and are reflected by time-varying properties such as intermittent synchronization/Mainardi L. T. et all, IEEE Engineering in Medicine and Biology, Vol.16,No 6, pp.64–75, 1997/That means that metabolic and homeostatic oscillations do not interfere or summarize, and they are synchronized/Landa P. S. and Rosenblum M. G., Priroda, No 8,pp.18–27,1992/. Intermittent coupling in normal function of biological systems is displayed by a dynamic hierarchy of biological rhythms that continuously vary in time. The struggle between the time-domain processes of separate mechanisms on the one hand to persist in their intrinsic behavior and, on the other hand, to pursue the coordinated by non-linear mechanisms time-domain rhythm leads to a phenomenon known as a dynamic chaos/West A. J., *Fractal Physiology and Chaos in Medicine*, NY, 1990/.

Injury and disease cause disturbances of different physiological rhythms and alter the general structure of dynamic chaos. The key of such chaotic behavior of biological systems lies in a fact that they have extreme sensitivity to the temporal behavior of a perturbing factor acting simultaneously on several homeostatic levels/Olsen L, F. and Degn H., Rev. of Biophysics, Vol.10, No 2, pp163–225, 1985/ Oscillations of such factor not being coordinated with the temporal dynamics of metabolic and homeostatic processes may effect at the moments when their energetic requirements may not be able to maintain. As a result, it initiates unspecific reaction of an organism directed either to restoring the initial state or to transformation in a new unpredictable state. Physical action such as ultrasound, electromagnetic waves, laser and X-ray radiation simultaneously effect several homeostatic levels of a biological system and not being coordinated with their temporal dynamics have low predictability of the treatment effect. Besides, predetermined doses that usually are used in physical, laser and radiotherapy are far from individual, and that markedly decreases the treatment effectiveness.

The biofeedback methods and systems for co-ordination an individual's physiologic functioning and applied physical action are well known in the art. Conventional biofeedback techniques can be classified in two groups. The first one involves a mental modifying of an individual's physiological functioning by providing "feed-back" of their physiological activities. Known instruments of this category provide indication of the heart rate/U.S. Pat. No. 4,450,843 issued May 29, 1984 to Barney et all; U.S. Pat. No. 5,007,430 issued Apr. 16, 1991/, brain waves/U.S. Pat. No. 4,031,884 issued Jun. 28, 1977 to Henzel et al/, blood pulse waves/U.S. Pat No. 4,450,843 to Barney et all; U.S. Pat. No. 5,475,725 issued Dec. 12, 1995 to Nakamura et al/. Biofeedback methods and systems of other type in this group convert measurable physiological activities of an individual into feedback signals comprising an auditory or visual stimulus/U.S. Pat No. 4,883,067 issued November 1989 to Knispel et al/.

These feedback techniques have well known limitations. The feedback signal normally indicates only a time average of the relevant physiological activity and has no direct effect on ongoing biological processes involved in a disease and, therefore, can not produce a true real time feedback control. Further, the pathway by which feedback signals control an individual's physiological functioning includes such low predictable parameter as emotional state of the individual. Besides, the success of the treatment sufficiently depends on education and professional skills of the instructor that learn the individual how to control physiological function.

Biofeedback techniques of second group have opposite direction of controlling and control the factor applied to the individual being treated. Various patents disclose these instruments. Most of them directly control the factors effecting only one ongoing process involved in a disease. U.S. Pat. No. 5,522,854 issued Jun. 4, 1996 to Ideker et al discloses a method and apparatus for biofeedback stimulating an implanted electrostimulator. Provided by monitoring the symphatetic and parasymphatetic nerve activity biosignals are processed to produce treatment through electric shock at the moments of detection of the states of high risk arrhythmia. Similar biofeedback system delivering electrical stimuli directly to cardiac tissue is disclosed in U.S. Pat. No. 5,447,520 issued Sep. 5, 1995 to Spano et al. According to this invention the timing of intervals between heart beat pulsation in response to a single stimulus intervention is performed during approximately 5 to 60 seconds. At this time the dynamic behavior of a chaotic regime is evaluated according to a special algorithm. At high risk moments of arrhythmia determined by this algorithm biofeedback signals control tissue stimulus injector.

An important advantage of these inventions is that they produce feedback signals in a real time. However, their application is limited by sensitivity to only one level of cardiac control, and controlling is provided only after a cardiac event has already occurred. Much more wider sensing or therapeutic vigilance with progressively higher degrees of therapy is disclosed by U.S. Pat. No. 5,749,900 issued May 12, 1998 to Schroeppel et al. The feedback signals are derived from comparison of evaluated numbers of the heart rate variability with previously stored one, and according therapy regimes are initiated.

All above described techniques related to the second group provide control of the physical factor effecting only one physiologic parameter, which is monitored. Being used for controlling the action of multilevel action in physical, laser and radiotherapy these techniques do not provide synchronization of the action simultaneously with several homeostatic levels of an organism and, therefore, cannot enhance reproducibility of the treatment effect and effectiveness of the treatment. Perhaps the only one feedback system, which is able to synchronize physical factor of multilevel action is disclosed by USSR Patent 1,481,920 issued Nov. 14, 1986 to Zaguskin et all. According to the patent the cell biorhythms are determined at the first step. Then the physical action applied to the biological object is modulated by at least three frequencies selected from a measured cell rhythm spectrum. It is believed that synchronization of the factor with several frequencies of the cell rhythm is adequate to synchronization to rhythms of all homeostatic processes. Not dealing with biological aspect of this method it should be just mentioned that measurement of the cell rhythms in vitro principally prevents biofeedback control in a real time.

In view of the foregoing, there has been no biofeedback method or apparatus for synchronization of the physical factor applied to a subject for treatment purposes with biological rhythms of several homeostatic processes simultaneously.

It is believed that co-ordination of the interaction between homeostatic rhythms and their intermittent synchronization is reflected in peripheral blood pulse circulation/Goldberger A. L. and West B. J., *Fractals in Physiology and Medicine*, Yale J. of Biology and Medicine, Vol.60,pp421–435, 1987./ Being a multisystem blood supplies oxygen and nutrients and clear metabolic waste products. A complex neural and neuro-hormonal mechanisms controlled by Central and Autonomic Nervous Systems co-ordinate the peripheral blood flow with rhythms of metabolic and homeostatic processes/Bayevsky R. M., *Prognosis of Boundary States between Norm and Pathology*, Medicine, Moscow, 1979./ Thus, blood flow through the body is adjusted to the momentary harmony of biological rhythms by combination of regional and higher level control mechanisms, and any factor, which is synchronized with blood flow will be co-ordinate to it too. Unfortunately, there has been no biofeedback technique available for synchronization the factor applied to a subject with cycles of its peripheral blood flow.

Usually these cycles are derived from a pulsatile component (a.c.) of the photoplethysmographic (PPG) signal sensing from a subject. Along with a small a.c. component attributable to light attenuation changes resulting from blood volume changes during cardiac cycle the PPG signal contains a large nonpulsatile component (d.c.) regarded to light attenuation produced by fixed elements in the tissue. Because the d.c. component does not contain information about blood flow it has to be removed of the signal. In conventional biofeedback technique the d.c. component is subtracted by blocking with a capacitive blocking element. Such elimination of the d.c. component cause—strong distortion of the remaining a.c. component and the distortion depends on the a.c. amplitude variations. Thus, the distortion varies from a subject to subject and even from pulse to pulse. That makes locating the points of discrimination between different cycles in pulse wave of blood flow very hard.

Conventional pulse oxymeters are also used for the PPG signal and for locating the discriminating points/*Design of Pulse Oximeters*, Edited by J. G. Webster, Publ. By Institute of Physics Publishing, Bristol and Philadelphia, 1997L The signal for calculation of the blood oxygen saturation is derived from the same pulse wave. Along with removing me d.c. component of the signal by blocking/U.S. Pat. No. 4,305,401 issued Dec. 15, 1981 to M. Reissmueller et al/the U.S. Pat. No. 4,800,495 issued Jan. 24, 1989 to R. Smith discloses the pulse oxymeter with programmable elimination of the d.c. component by offset amplifier that offsets a portion of the d.c. component of the PPG signal. To achieve utilization of entire dynamic range of the current-to-voltage converter this pulse employs a complex procedure of signal digital construction-reconstruction. The primary problem of such elimination is that it leaves the a.c. pulsatile component centered not enough close to zero level. That makes it hard to identify the discriminating points in pulse wave. This problem remains also when elimination is performed accordingly by the U.S. Pat. No. 4,086,915 issued May 2, 1978 to Kofsky et. al.

SUMMARY OF THE INVENTION

Accordingly, it is an object of present invention to provide a method of and an apparatus for a bioresonance for individual coordination of physical factors applied to a subject for treatment purposes, which avoid the disadvantages of the prior art.

In keeping with these objects and with others which will become apparent hereinafter, one feature of present invention resides, briefly stated, in a method of and an apparatus for a biofeedback, in accordance with which a physical action is applied to a subject for treatment purposes in coordination of cycles of arterial blood pulse flow of a subject.

It is a further object of the invention to provide a method and apparatus for automatic individualization the dose of action of the applied action.

As it is well known the temporal dynamics of peripheral blood flow comprises cycles of arterial systolic upstroke and diastolic drain/Hole J. W., *Human Anatomy and Physiology*, Brown Company Publishing., 1982./Almost all factors being used in physical therapy, laser and radiotherapy such as ultrasound, electromagnetic waves, laser radiation, etc. are directed to restoring the cell process and tissue regeneration and require synchronization to systolic upstroke cycles. However, there exist some particular factors such as for example, X-ray, massage, which principally require synchronization with diastolic drain cycles due to direct (massage) or indirect effect on blood circulation (side effect of X-ray irradiation).

It is easy to show that synchronization of the physical action acting on a subject with the cycles of arterial pulse flow provides also an opportunity for automatic individualization the dose receiving by an organism. Generally under receiving by an organism dose D one understand the product of intensity of acting physical factor I by time of exposure t:

$$D = I\, t$$

In pulse mode the dose depends on the ratio $\eta$ of the pulse width $\tau$ to pulse period T:

$$D_p = I\, t\, \tau/T = I\, t/\eta$$

Synchronization makes parameters $\tau$ and T, and therefore the dose D individual. In this regard, simply by synchronizing the action applied to a subject with the subject's cycles of arterial blood flow an opportunity of automatic dose individualization is provided.

Being synchronized to a subject's cycles of arterial pulse bloood flow the physical action much less disturbs the hierarchy of homeostatic and metabolic rhythms and thus provide markedly more predictable and effective treatment.

It is an additional object of the invention to provide a method and apparatus for synchronization of two action simultaneously applied to the individual being treated with different cycles of its arterial pulse blood flow.

It is another object of the present invention to provide a signal conditioning circuit with automatic elimination the d.c. component prior the amplification.

In keeping with these objects and with others which will become apparent hereinafter, one feature of the present invention resides in a new method and apparatus for synchronization the physical action applied to a subject for treatment purposes among other applications in accordance with systolic influx or/and diastolic drain cycles of subject's pulse blood flow. As it was described above, the synchronization to the cycles of subject's peripheral blood flow co-ordinates the physical factor with temporal dynamics of homeostatic rhythms that decrease occurring negative homeostatic reactions on treatment. Besides, the synchronization provides automatic individualization of the dose of the physical factors action on a living body that also sufficiently enhances reproducibility and effectiveness of the treatment.

The present invention is based on locating the points of discrimination between systolic upstroke and diastolic descent portions of the pulse wave derived from the PPG signal. Although the present invention describes a method and apparatus which employ the PPG principle of blood pulse wave detection, it in no case is not intended to be limited only by photo-electrical detection of the pulse waves. Many types of pulse wave detectors such as piezoelectric transducers, crystal microphones, Doppler ultrasound, etc. can be used to detect the pulse wave.

In the present invention the synchronization is provided by controlling a source of the physical action by means of synchronous to systolic upstroke and diastolic descent time in each pulse wave feedback signals derived from time intervals between the points of discrimination these cycles. In a preferred embodiment the discriminating points are the points of maximum systolic upstroke rate and systolic peak points.

The method of the present invention comprises the steps of sensing the arterial blood pulse waves, selecting in each pulse wave the systolic blood influx and diastolic blood drain cycles, generating in the first channel biofeedback signals synchronously to systolic upstroke time and in the second channel biofeedback signals synchronously to diastolic drain time, synchronizing the physical action by controlling by biofeedback signals from the first or second channel.

In a preferred embodiment the sensing of arterial blood pulse waves is utilized by deriving the PPG signals from a sensor disposed in contact with the body at the nearest to the affixed area location where the pulse waves can be detected. The method involves locating in each pulse waveform the points of maximum rate of systolic blood influx and systolic peak points by differentiating twice the blood pulse waveform with respect to time and selecting the systolic upstroke time intervals by locating the zero-crossings of the first and second differentiated waves. Generating the biofeedback signals is utilized by generating square pulse signals with the pulse width equal to the time of corresponding cycles and being synchronous to the pulse waves.

According to the present invention an apparatus locates the discriminating points in the pulse waveform of the PPG signal derived by a sensor of either transmission or reflection type, and generates feedback square waves synchronously to systolic upstroke or diastolic descent times. For accurate locating of the discriminating points an improved signal conditioning circuit which is automatically removes not pulsating d.c. component of the signal prior amplification is provided.

The invented unique biofeedback method and apparatus provide synchronization and dose individualization of a wide variety of the physical action applied in physical therapy laser and radiotherapy and enhanced effectiveness and predictability of treatment over wide spectrum of diseases. The apparatus is relatively simple and cheap and can be used as an interface to any of existing physical therapy, laser and radiotherapy equipment. The benefits of the invention are particularly high when it is used for combined treatment by two physical factors simultaneously such as, for example, radiotherapy along with mechanical pulse squeezing of the blood from targeted area. Synchronization of the irradiation and squeezing cycles with blood diastolic drain intervals and additional laser biostimulation synchronously to systolic influx time allow to increase available dose of irradiation and markedly enhance the success of the treatment.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 12 is a graphical illustration of the signals produced by a conditioning circuit according to the preferred embodiment;

DESCRIPTION OF PREFERRED EMBODIMENTS

Figure 1:
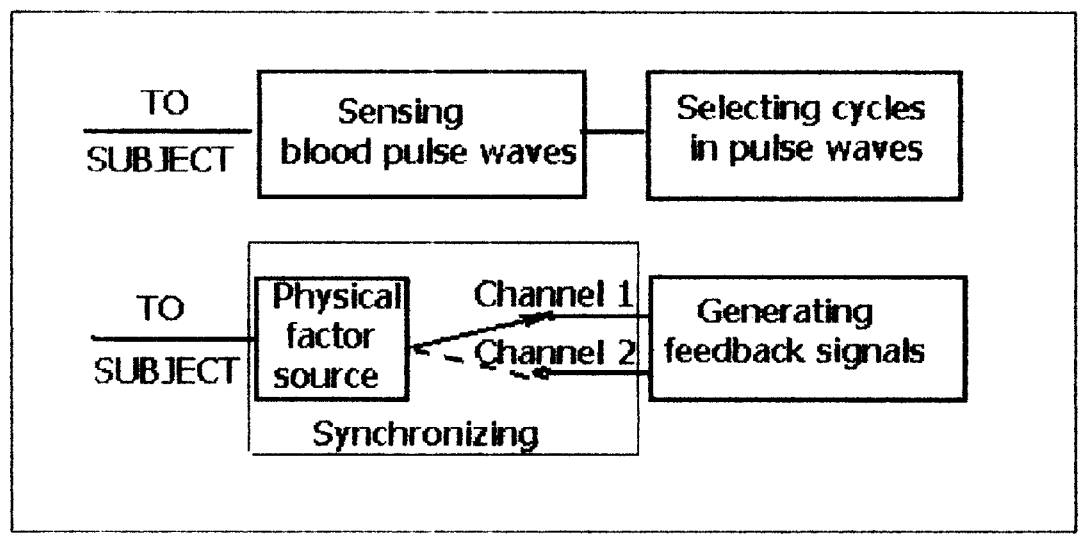
FIG. 1 shows a sequence of steps of the process of synchronization the physical factor applied to the individual being treated according to the invention.

A new method and apparatus are provided for synchronization the physical factor applied to a subject with treatment purposes among other applications with different cycles of arterial pulse blood flow. FIG. 1 shows a sequence of steps of the process of synchronization. The method involves sensing the peripheral blood pulse waves, selecting in each pulse waveform the systolic upstroke and diastolic descent cycles, generating feedback controlling signals synchronously either systolic upstroke or diastolic descent time and synchronization of the physical action applied to the individual being treated by controlling the source of applied physical action or appropriate modulator. The selection of the cycles of blood flow comprises locating the points discrimination between these cycles. Generating the feedback signals is utilized by deriving square pulse signals with pulse width equal to the time of corresponding cycles and being synchronous to the discriminating points. As it is illustrated in FIG. 1, the synchronization is utilized by controlling the physical action by feedback signals from the first or second channel. Controlling the physical action means modulating the source of the action or an external modulator by feedback signals from the first or second channels. It is assumed that the output of the source of the action is proportional to the intensity of feedback signals (if the feedback signal is zero, than the factor is "Off", if the feedback signal is not zero, than the factor is "On"). In a particular case of factor, which cannot be turned On and Off by controlling signal the appropriate modulator is used to the same effect.

Figure 3:
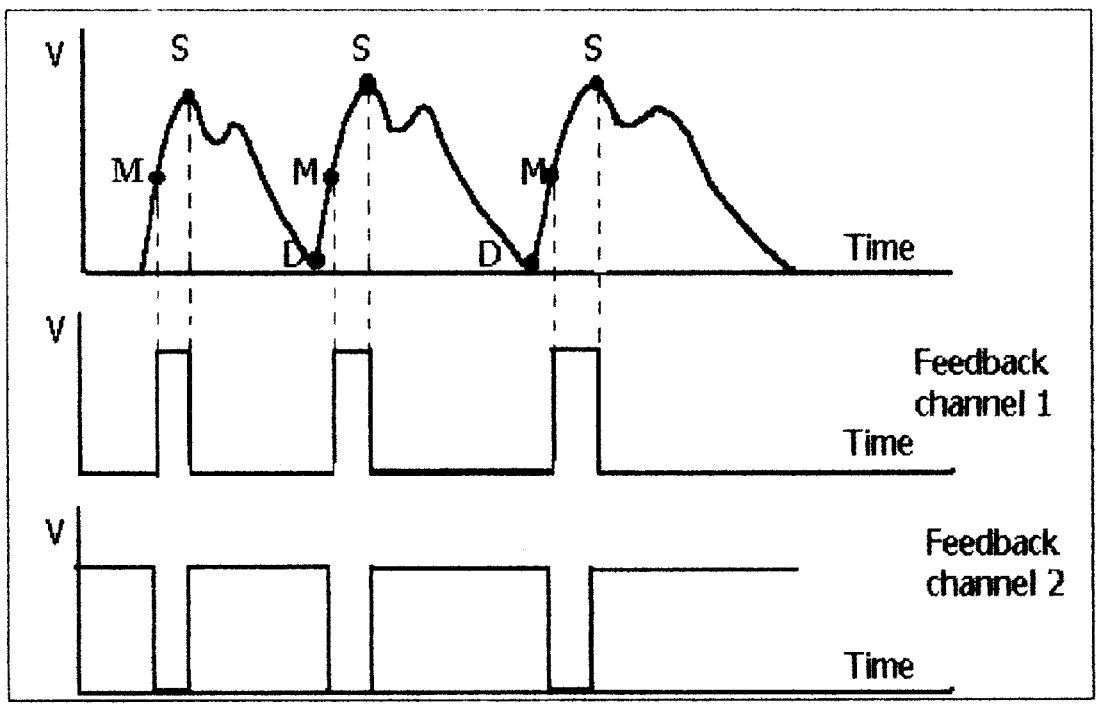
FIG. 3 illustrates the location of the discriminating points in pulse wave and corresponding signals in the output channels.
Figure 2:
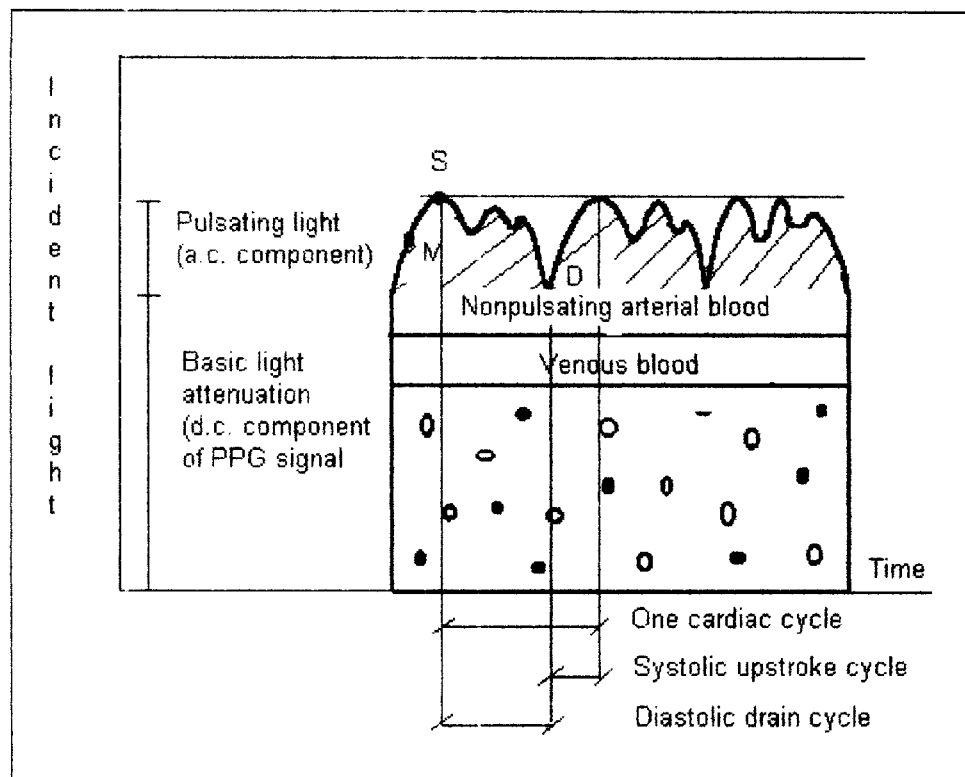
FIG. 2 shows the cycles of arterial pulse blood flow and illustrates formation of the photoplethysmographic signals.

Since the PPG method enables to directly detect the blood pulse waves, it is used in preferred embodiment for sensing arterial blood pulse waves. However, the invention is not intended to be limited to any specific kind of sensor. Basically, as it is illustrated in FIG. 2, the PPG method involves sensing the effect of blood in tissue on the light passing therethrough. Arterial pulsation increases blood volume in tissue during systole and decrease during diastole. Because of light attenuation by blood absorption and scattering, the light emerging from the tissue is inversely proportional to the volume of blood in tissue/Grimblatov V. Proc. SPIE, Vol.3253, pp119–127, 1998/. Thus, the emergent light intensity will contain a pulsatile component (a.c.) caused by pulse waves of arterial blood and a constant component (d.c.) related to absorption and scattering of tissue inhomogeneities and chromophores such as bone, skin pigmentation, venous blood, etc. Each arterial blood pulse wave consists of systolic influx and diastolic drain cycles, which are limited by systolic onset and peak points on pulse waveform (correspondingly the points D and S in FIG. 2). These points are used in photoplethysmographic techniques that utilize the monitoring of blood pulse waves/U.S. Pat. No. 4,928,692 issued May 19, 1990 to Goodman et al). However, accurate location of systolic onset points is highly dependent upon valid pulse waveform typically detected by a sensor disposed on extremity or on the nose or ear. The pulse waveform can be distorted by motion of the body site where the sensor is affixed. Different approaches to elimination motion artifact have developed and various methods and instruments have been disclosed, but the problem still exist/Webster J. G., *Design of Pulse Oximeters*, IOP Publishing, 1997/. The systolic onset points are the most difficult for selecting because of sharp changing in the direction of the slope of the waveform. The use of an additional electrocardiograph (ECG) for gating the expecting moments of occurrence of these points (U.S. Pat. No. 5,485,847 issued Jan. 23, 1996 to Baker) or independent motion detector (U.S. Pat. No. 5,226,417 issued Jul. 13, 1993 to Swedlow) is not effective enough because the time delay between ECG waves and blood pulses varies individually and makes selection complicated and expensive. The other disadvantage of this approach is that selecting these points sharply limits the rate of changing of applied physical factor because any change of the factor with rate higher than the rate of blood influx will disrupt synchronization. In a preferred embodiment, it is used selecting the points of maximum systolic influx rate along with systolic peak points (points M and S in FIG. 2). Along with low sensitivity to motion artifact these points allow to sufficiently increase the rate of available changes of the applied factor and are easy for reliable detection. Accordingly, the generating of feedback signals corresponding to selected points comprises:

generating in the first channel electrical pulses with duration and occurrence equal to the duration between points of maximum rate of systolic influx and systolic peak points (intervals M–S in FIG. 3) and synchronously to the moments of occurrence of the points of maximal rate of systolic influx;

generating in the second channel electrical pulses with duration and occurrence equal to the duration between systolic peak points and points of maximal rate of systolic influx (intervals S–M in FIG. 3) and synchronously to the systolic peak points.

Figure 4:
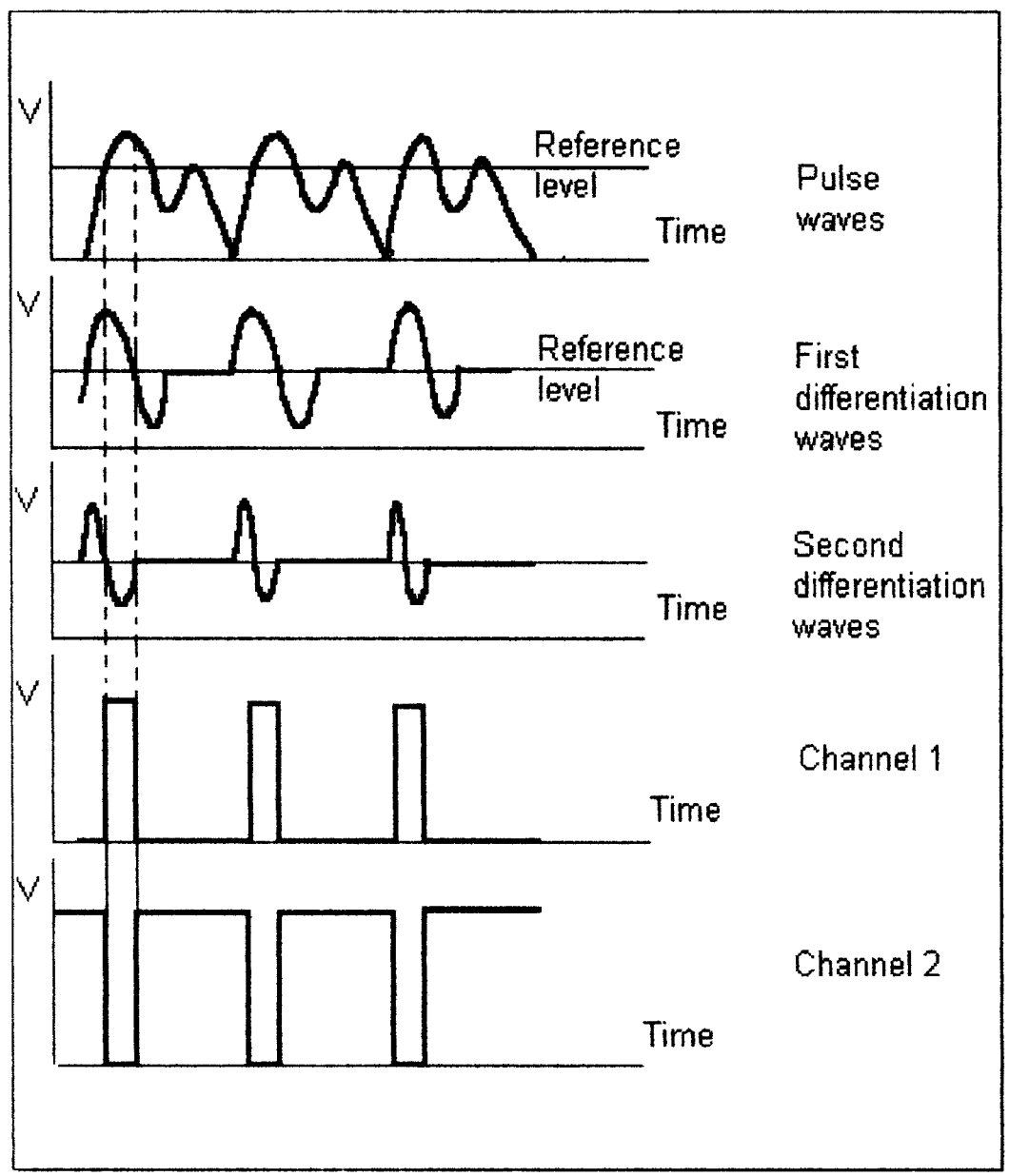
FIG. 4 is a graphical illustration of the signal transformation to according a preferred embodiment of the invention.
Figure 7:
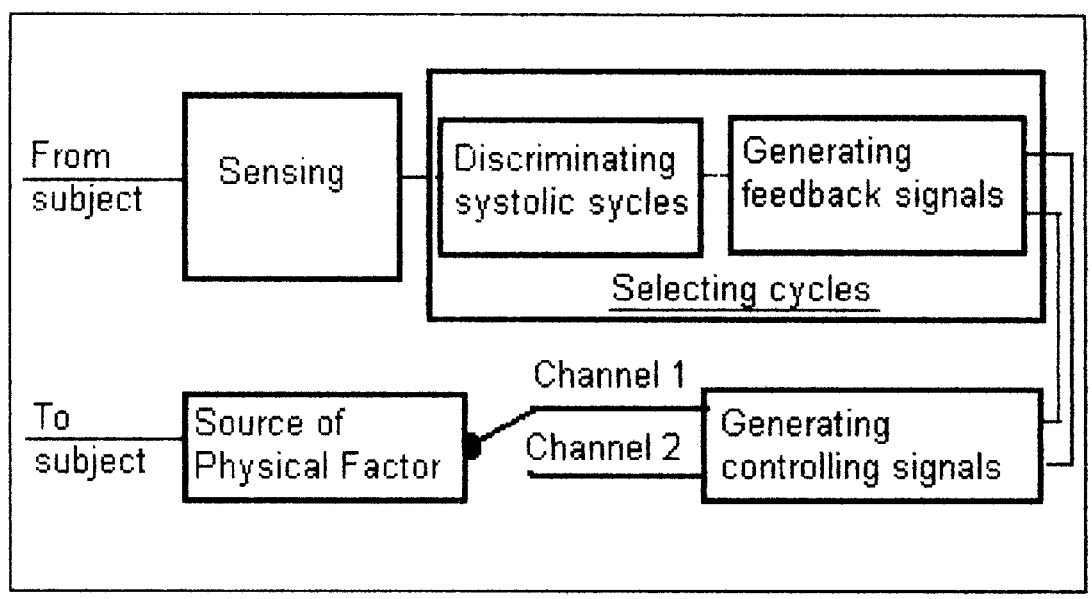
FIG. 7 is a detailed block diagram of a sequence of steps involved in the method of synchronization according a preferred embodiment.
Figure 5:
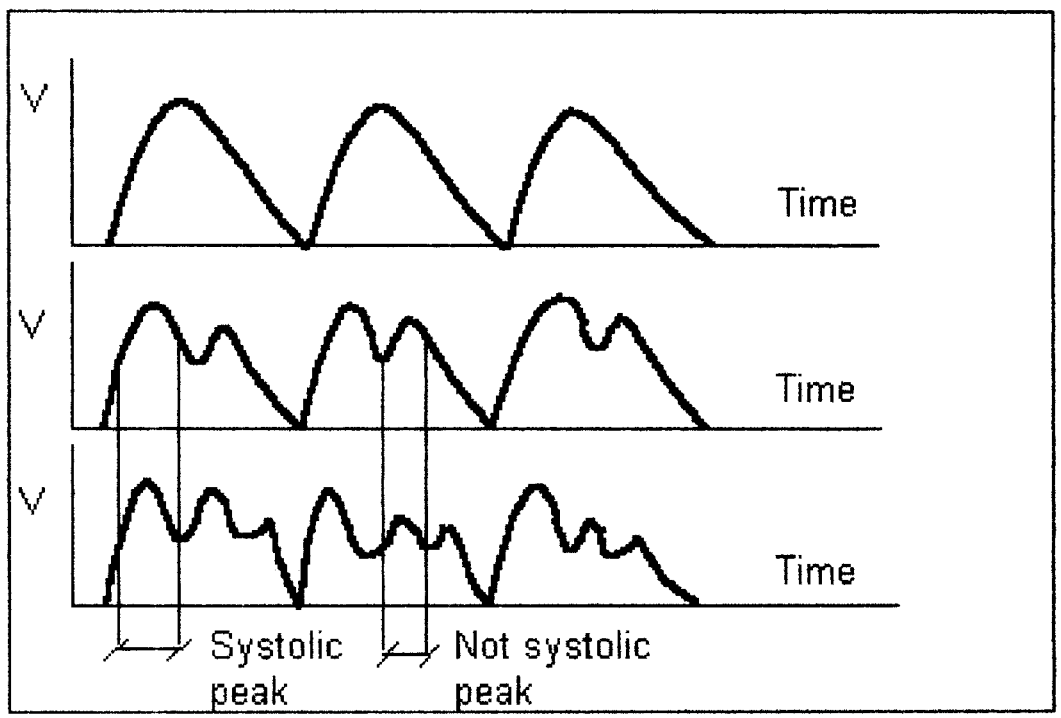
FIG. 5 shows different types of arterial blood pulse waveforms.
Figure 6:
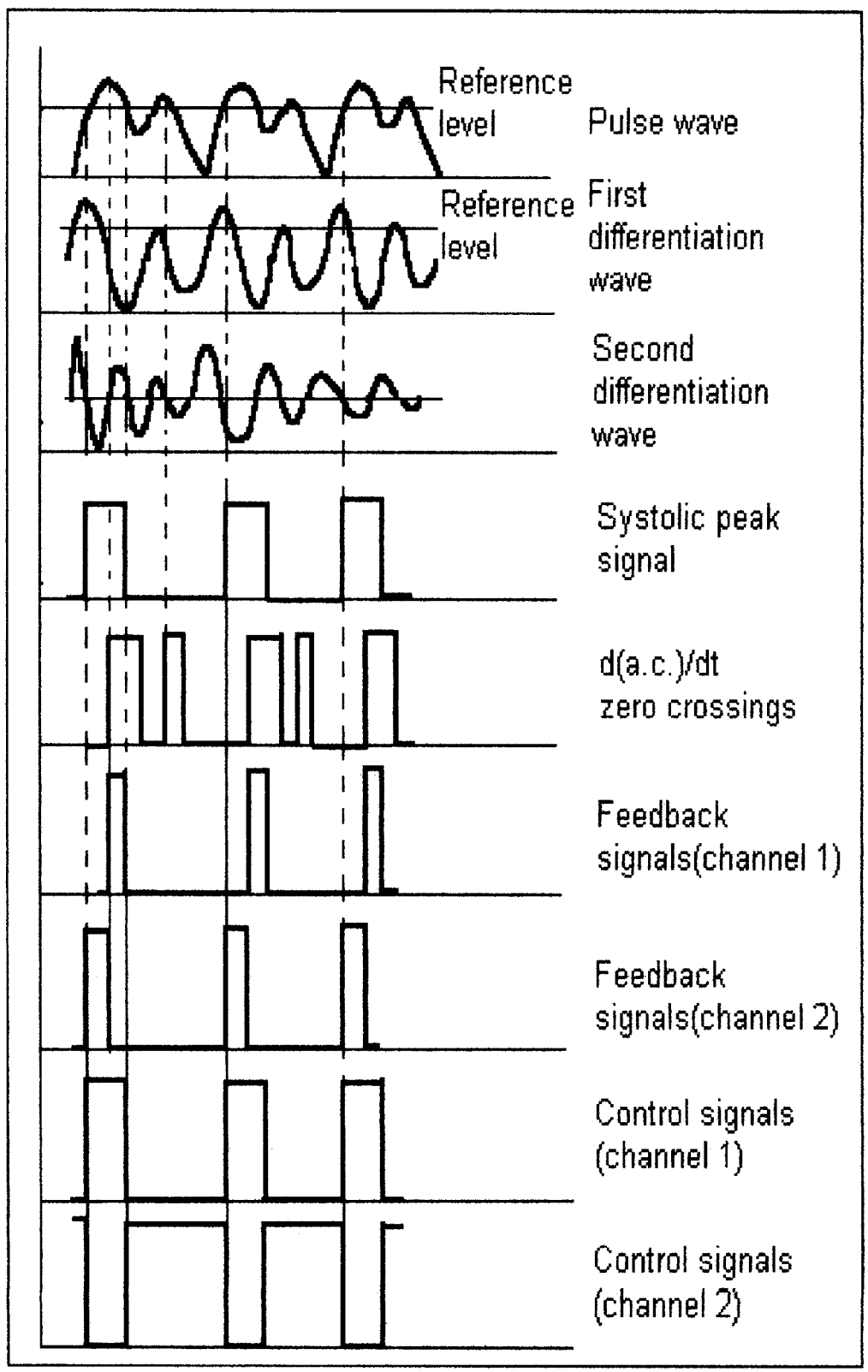
FIG. 6 is an illustration of translating the waveforms of the signals according to a preferred embodiment.

Locating these discriminating points involves differentiating twice the pulse waveform with respect to time and locating these points as the points of zero-crossing of the first and second derivatives as illustrated in FIG. 4. Going from our study based on Kubelka-Munk theory (Grimblatov V. et all, Proc. SPIE, Vol. 2082 pp. 112–119,1993) the derivatives of the pulse waveform are substantially independent of the d.c. component and therefore, are less sensitive to motion artifacts. Published data and our study prove that pulse waveforms may have not only a systolic peak (see FIG. 5). In a preferred embodiment, to discriminate systolic peak from not systolic the amplitudes of the pulse waveform and first derivative wave are compared with predetermined reference signals (see FIG. 6). Detailed block diagram of a sequence of steps involved in the method according to the preferred embodiment of the present invention is shown in FIG. 7.

Another embodiment of the invention is based on selecting the cycles of arterial pulse blood flow by locating onset and peak systolic points on the pulse waveforin (points D and S in FIG. 2).

Figure 8:
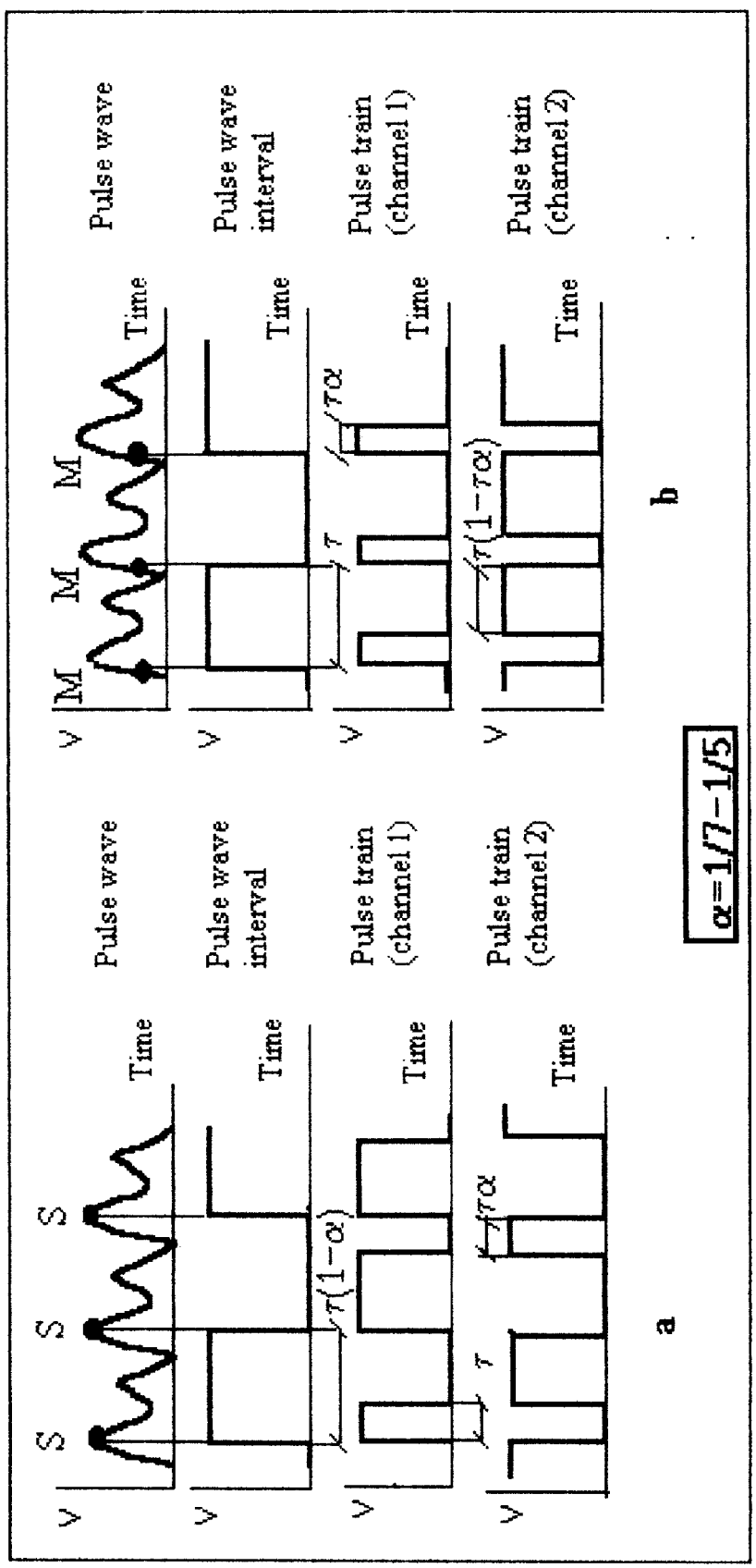
FIG. 8 illustrates the embodiment of synchronization by locating in pulse wave of either systolic peak points or points of maximum of systolic upstroke rate.

Further embodiment of the invention is based on discriminating between systolic and diastolic cycles by means of determining the average time intervals between homologous points on pulse waveform and dividing the interval in a predetermined proportion. Our empirical observation confirm that the ratio of systolic to diastolic time is relatively stable and its variations from subject to subject fall in a consistently narrow region from 1/7 up to 1/5. That allows to provide discrimination between systolic and diastolic cycles simply by selecting pulse wave intervals. As illustrated in FIG. 8, it can be utilized either by locating only systolic peak points S on pulse waveform or only points of maximum. systolic upstroke rate M. Accordingly, the first type of this embodiment of the invention is based on locating S points by differentiating the pulse waveform with respect to time. After locating the peak points S next step is dividing the time interval between located points in a predetermined proportion for establishing two trains of pulses in two channels with pulse width ratio being equal to the predetermined proportion (see FIG. 8). In utilizing this embodiment of the invention on a subject initially an average pulse rate is derived by one of the conventional methods and an average pulse wave interval is calculated. Synchronizing the occurrence of pulses in channel 2 with the moments corresponding to S-points, and synchronizing the occurrence of pulses in channel 1 with the ends of pulses in channel 2 a synchronization of the biofeedback controlling signals with the cycles of arterial pulse blood flow is achieved.

The present invention also includes an apparatus utilizing the method of present invention. Referring the overall apparatus block diagram shown in FIG. 9, an apparatus 0 includes a sensor 1 further comprising a probe 6 including a light source 13 and a photodiode 15, a signal conditioning circuit 7, a signal processing circuit 2 comprising a first and a second peak detectors 8 and 9, a controlling circuit 3 comprising a trigger 10 and signal power amplifiers 11 and 12, and a power supply 4.

The first component of the apparatus to be discussed in detail is the sensor 1. The sensor includes a probe 6 and a signal conditioning circuit 7. The probe employs a light emitting diode (LED) 13 to produce incident on blood content tissue 14 light and a photodiode 15 to detect light attenuated by transmitting through the tissue at infrared or other wavelength. The probe prevents orientation of the LED and photodiode with respect to a suitable portion of a subject's body. In the preferred embodiment LED emits light at 830 nm. However, the invention is not intended to be limited to any specific wavelength of light produced by LED or selected from a regular light source by special filtering. The LED is supplied by current from a power supply 4.

Figure 10:
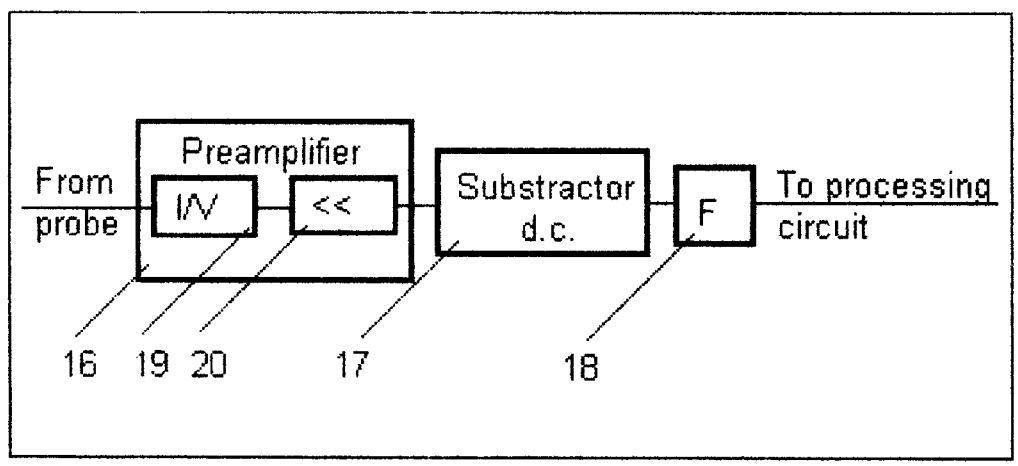
FIG. 10 is a block diagram of conventional conditioning circuits.

The signal from the photodiode is received by signal conditioning circuit 7. This circuit is responsible for three aspects of signal conditioning and as typically employed by pulse oxymeters, comprises three separate block as a is shown in FIG. 10. First, amplifier 16 amplifies signal from photodiode 15. Next, subtractor 17 removes from the signal the d.c. component, which does not contain information about pulse waves. Third, filter 18 eliminates form the signal the noise of various nature. Known in the art of PPG preamplifiers typically include a differential current-to-voltage amplifier 19 and a single-ended amplifier 20 (U.S. Pat. No. 4,800,495 issued Jan. 24, 1989 to R. Smith). Since photodiode generates an output current, the amplifier 19 translates this current into a voltage with amplification by single-ended amplifier 20. The primary problem with conventional preamplifiers is that they amplify both components of the signal from photodiode, small a.c. component attributable to light attenuation changes resulting from blood volume changes during the cardiac cycle, and a large d.c. component considered for light attenuation produced by fixed elements in the tissue and not containing information about blood flow. Amplifying the substantial nonpulsatile component use up most of the dynamic range of the differential amplifier and saturates the gain. In this regard in order to provide needed amplification of the a.c. signal the elimination of large d.c. component is necessarily. A subtractor 17 accomplishes this removal. Conventional subtractors removes the d.c. component of signal by blocking with a capacitive blocking element (U.S. Pat. No. 4,759,369 issued Jul. 26, 1988 to Taylor et al) or by eliminating a substantial offset portion(U.S. Pat. No. 5,259,381 issued Nov. 9, 1993 to Cheung et al.,; U.S. Pat. No. 4,407,290 issued Oct. 4, 1983 to Wilber). Blocking the d.c. component by a capacitor partially differentiates signal and, therefore, substantially distorts the waveform of the pulse wave. These distortions depend on amplitudes of both components and vary even from a pulse to pulse. For this reason such devices can not provide the necessary accuracy of discriminating the cycles of pulse waves.

The removal of the d.c. component of the signal in prior art devices by offset voltage has two main disadvantages. First is that they eliminate the d.c. component after signal amplification and, therefore, do not resolve the above mentioned problem of gain saturation. Second disadvantage is that in the manner how the d.c. component is removed by offset voltage leaves the a.c. component . substantially out of zero level. That poses serious problem for accurate discrimination cycles in pulse wave.

Figure 11:
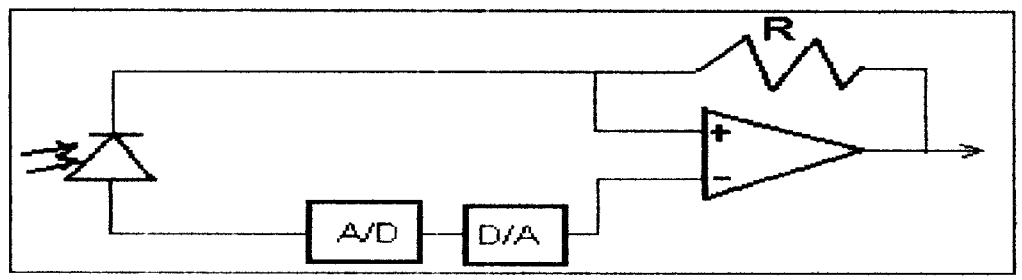
FIG. 11 is a schematic diagram of a conventional subtractor the d.c. component of the signal prior to amplification.

The only subtractor that provides automatic elimination of d.c. component of signal prior to being amplified is disclosed in U.S. Pat. No. 4,086,915 issued May 2, 1978 to H. Kofsky. The particularity of the d.c. component elimination disclosed in this patent can be illustrated by a circuit in FIG. 11. Referring to this figure, the signal from photodiode is applied in parallel to the plus terminal of differential amplifier and to the input of analogue to digital converter (AAD). In the A/D converter, the amplitude is converted to a digital word which is then converted back to an analogue signal in D/A converter, whose output is connected to the negative terminal of the amplifier. In the arrangement according to this patent the A/D converter is a low resolution converter with resolution less than the order of the a.c. amplitude. In the operation of the circuit it is assumed that the low resolution portion of the composite signal $I_{pd}$ is always and entirely due to the d.c. component. Although this is not rigorously true, with this assumption the circuit provides an output signal sufficiently indicative of the a.c. component as given by $$V=I_{pd}(1-K)R_f$$

where $R_f$ is feedback resistance, and K is relative resolution of the A/D.

The main problem here is that for some reasons the entire signal varies from subject to subject and from pulse to pulse. That overdrives the A/D converter and requires to make less offset voltage. That immediately leaves the a.c. component out of zero level and as was discussed above makes hard to discriminate cycles in pulse wave.

Figure 12:
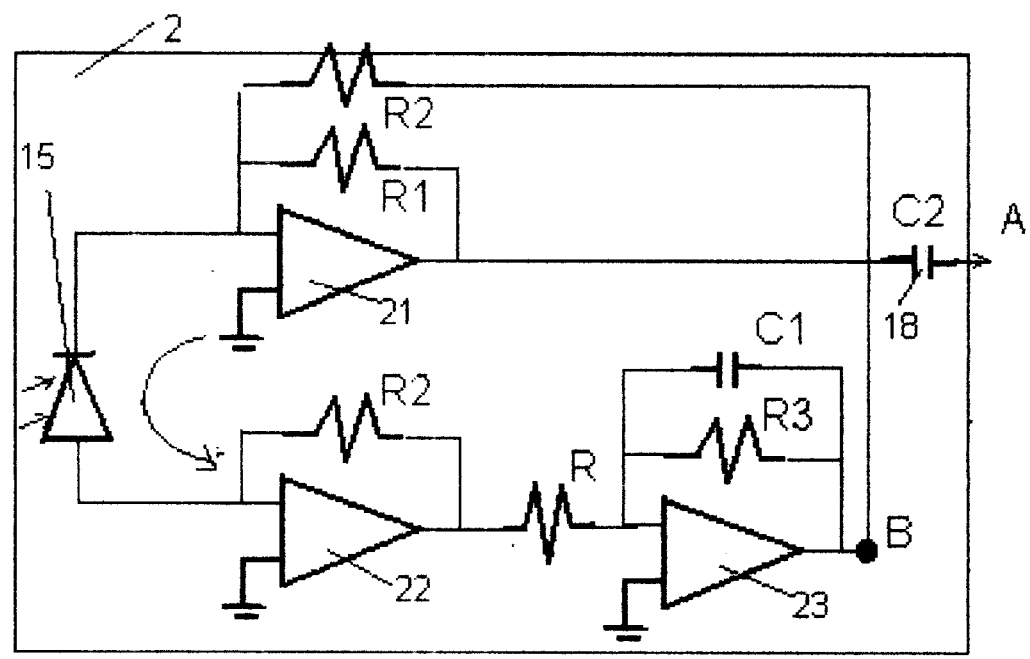
FIG. 12 is schematic diagram of a preferred embodiment of signal conditioning circuit.

Adoption of the signal conditioning circuit 2 according to a preferred embodiment of the present invention as it is shown in a schematic diagram in FIG. 12 enables to overcome the problem. As shown, a signal from a photodiode 15 is applied to negative terminals of a first and a second differential amplifier 21 and 22. The output of differential amplifier 22 is then supplied to the negative terminal of an inverter-filter 23. The signal outputted from the amplifier 23 is applied to input of the amplifier 21 through a feedback resistor $R_2$.

Since the signal of photodiode 15 is a current $I_{pd}$, it drives inputs of amplifiers 21 and 22 in different directions. Current flowing through the feedback resistor Rn creates a voltage at the output of amplifier 22 that is proportional to the light intensity as given by $$V_{pd}=(-I_{pd}).(-R_{f2})=I_{pd}.R_{f2}$$

Here $V_{pd}$ is a compose signal including both the a.c. and the d.c. components. This signal then is supplied to an inverter-filter 23. The capacitor C, and feedback resistor $R_{f3}$ create a filter, which blocks the a.c. component of the signal. So, the output voltage consists of only the d.c. component as given by $$V_{d.c.}=-(-I_{d.c.}).(-R_{f3})=I_{d.c.}.R_{f3}$$

Through the resistor $R_2$ this compensation voltage is fed to the negative input of the current-to-voltage amplifier 21 to which is directly connected the output of a photodiode 25. Thus, the current inputting into this terminal is given by $$I_{in}=I_{pd}-I_{d.c.}=I_{pd}-V_{d.c.}/R_2=I_{a.c.}$$

and contains only the a.c. component.

Figure 13:
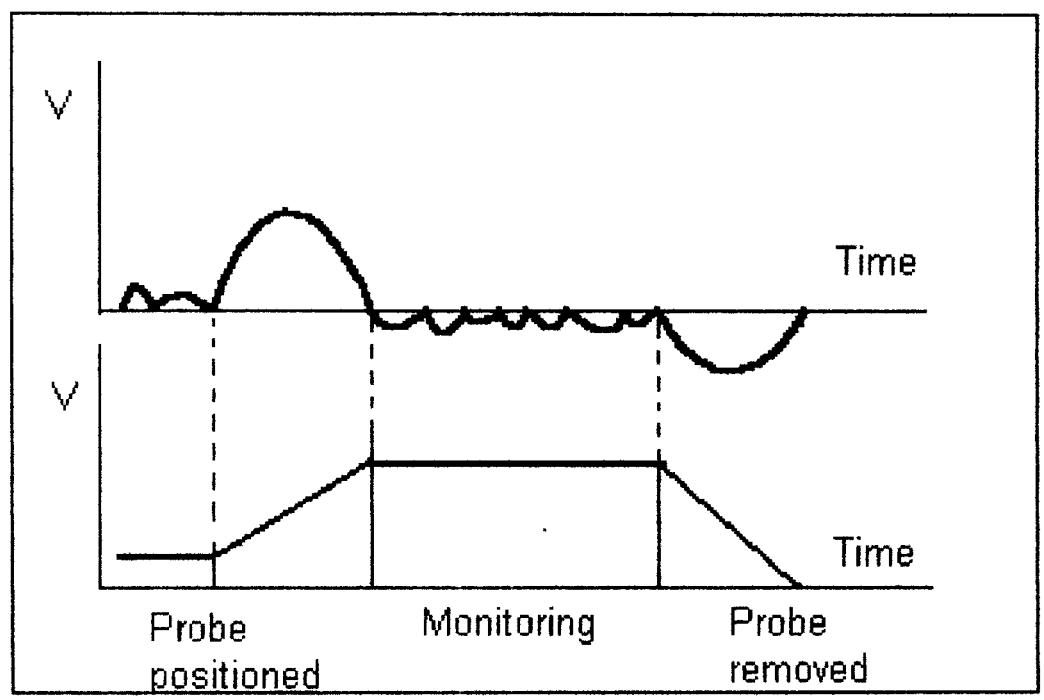
FIG. 13 is a graphical illustration of the signals produced by signal conditioning circuit according to a preferred embodiment of the present invention.

The signal translating by a signal conditioning circuit according to a preferred embodiment is illustrated in FIG. 13. Before the probe being positioned on a subject the voltage from the photodiode is zero and the compensation voltage is determined only by ambient light, which is made negligible by design of the probe. As the probe has positioned, the a.c. signal occurs along with growing of the voltage compensating the d.c. signal. So the elimination of the d.c. component of the signal is automatically provided prior the a.c. signal being amplified. That enables to use entire dynamic range of a current-to-voltage amplifier 21 for the a.c. amplification. Another benefit of this configuration is the automatic bringing the a.c. signal to zero-level voltage. That makes much easier accurate discrimination of the cycles in pulse waves. For elimination of the noises of various nature and smoothing the signal waveform the selected a.c. component further is fed to a filter 8, which typically is a low pass amplifier. Compensating voltage can be also used for indication of the correct probe positioning by comparison with a predetermined level $V_0$. When $V_{d.c.}>V_0$, a special comparator allows the sensor to operate.

The output of the signal conditioning circuit 3 is next inputs to a signal processing circuit 2 for selecting in each inputting pulse wave the points of discrimination between systolic upstroke and diastolic descent portions. This circuit has two peak detectors 8 and 9 that output two trains of square waves corresponding to the moments of occurrence of the located discriminating points.

Figure 14:
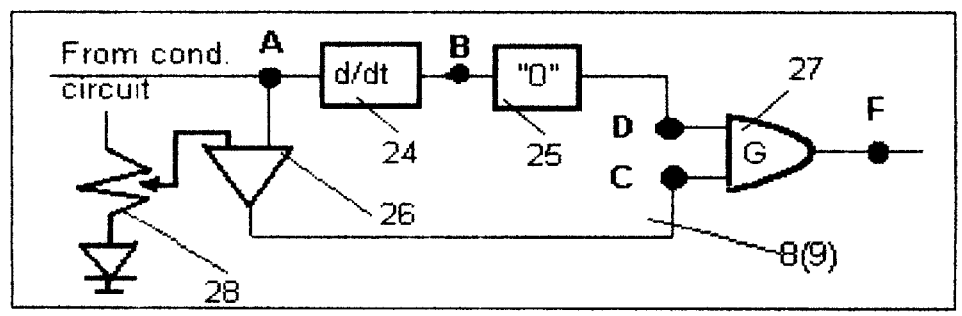
FIG. 14 is detailed block diagram a preferred embodiment of first peak detector.
Figure 15:
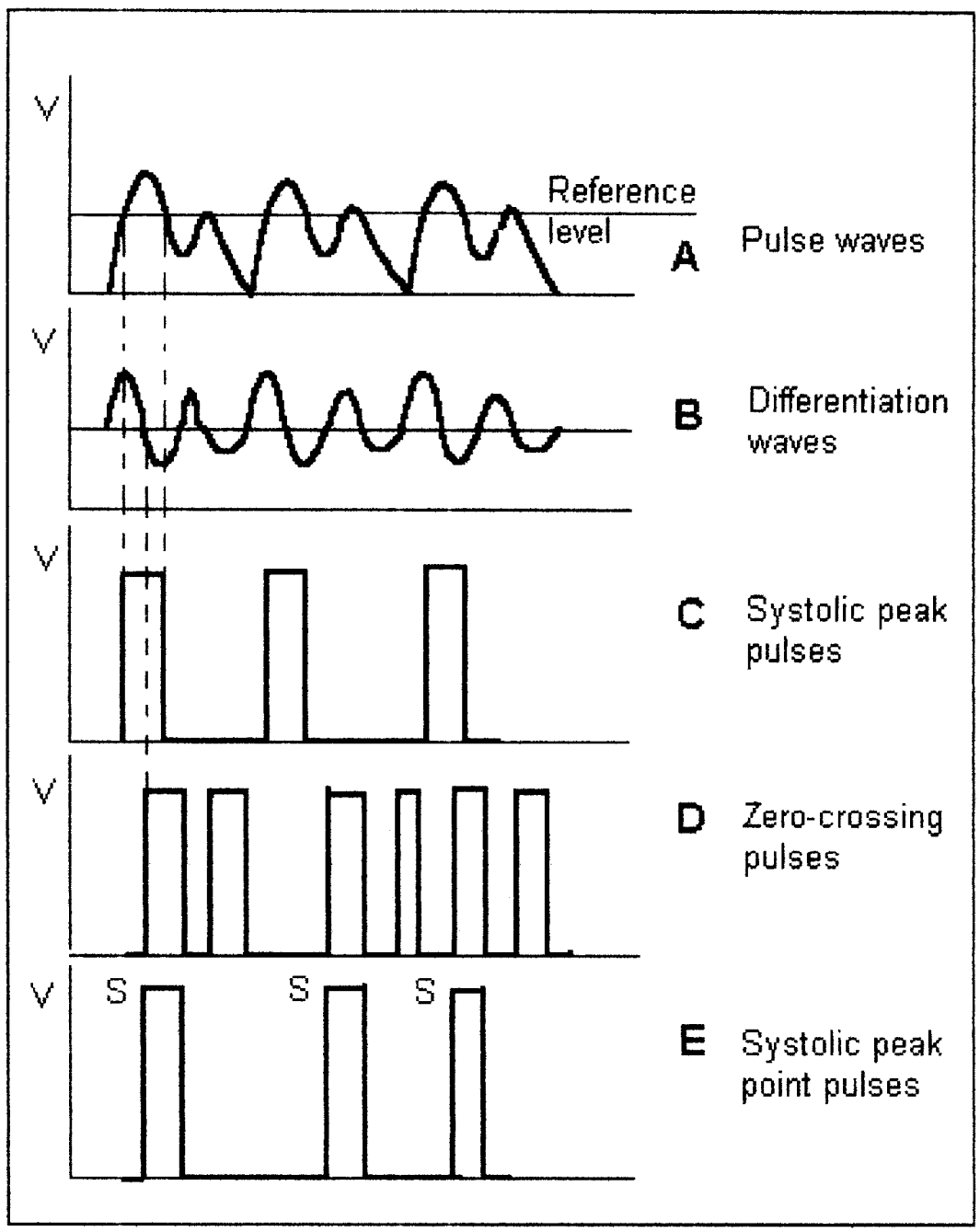
FIG. 15 is a diagram of waveform transformation useful in explaining of a signal processing by a first peak detector.

Referring to the drawing in more detail and to FIG. 14 in particular, the peak detectors 8 and 9 are identical as shown. Each of them includes a comparator 26, a differentiator 24, a zero cross detector 25 and a gate 27. The output of signal conditioning circuit 3 is fed simultaneously to the differentiator 24 and and comparator 26 of the peak detector S. After being differentiated with respect to time by differentiator 26 the differentiation wave signal inputs to zero-cross detector, which actually is a comparator to zero level reference voltage $V_{1r}$ and produces a train of square pulses corresponding to each zero-crossing of the differentiation wave. The voltage level comparator 26 compares amplitude of an input pulse wave signal voltage with a preset reference voltage (threshold level) and outputs a train of square pulses corresponding to systolic peaks only. Setting by resister 28 the threshold level enables individual adjustment of the detecting level for selection of systolic peaks of the pulse wave signal with any waveform. Two trains of square pulse signals are translated in a train of square pulse signals with leading edges corresponding to systolic peak points S in pulse waves by a gate 27. FIG. 15 is a graphical illustration of signal transformation by circuit FIG. 14.

Figure 16:
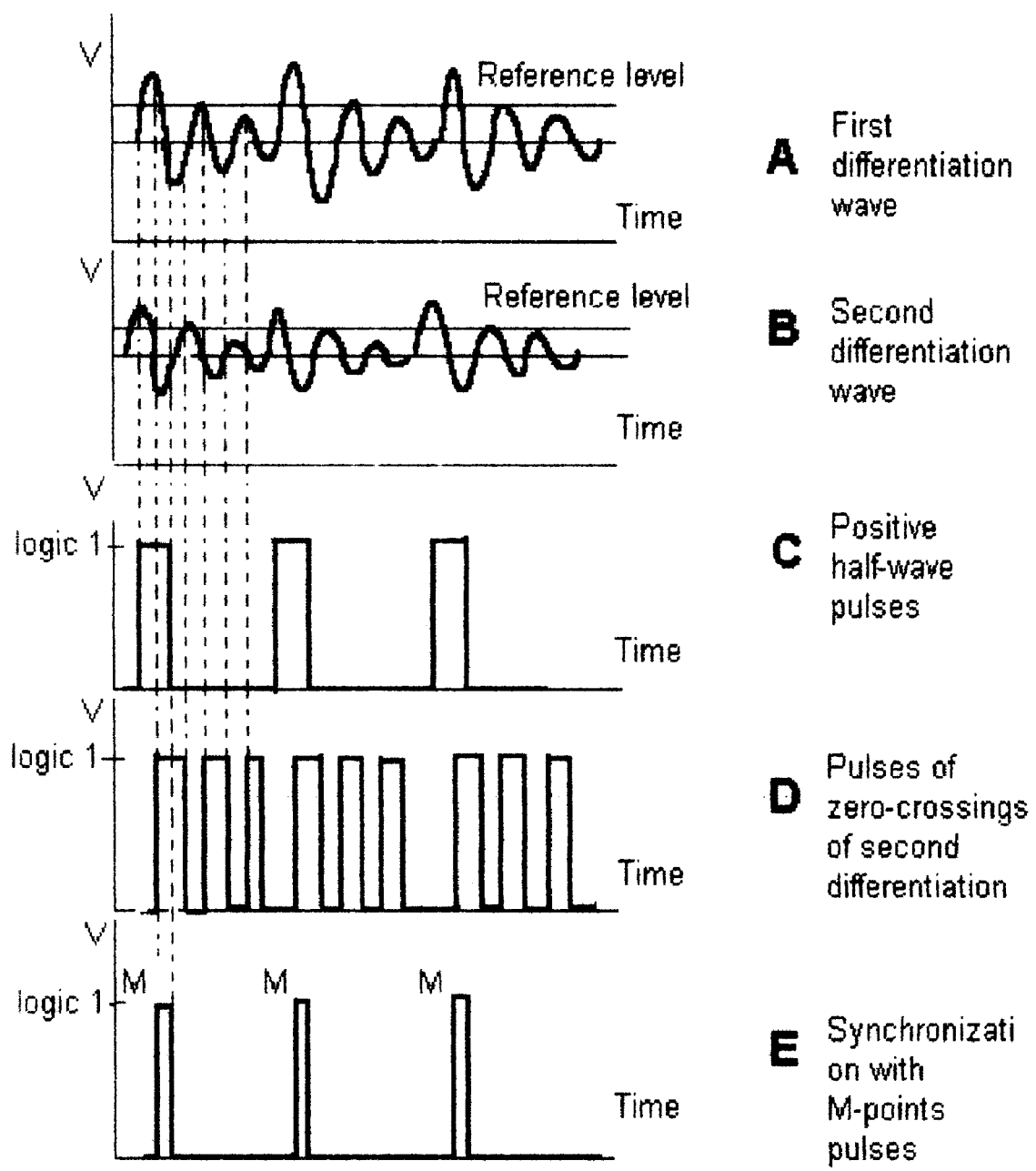
FIG. 16 is a diagram of waveform transformation useful in explaining of a signal processing by a second peak detector.
Figure 17:
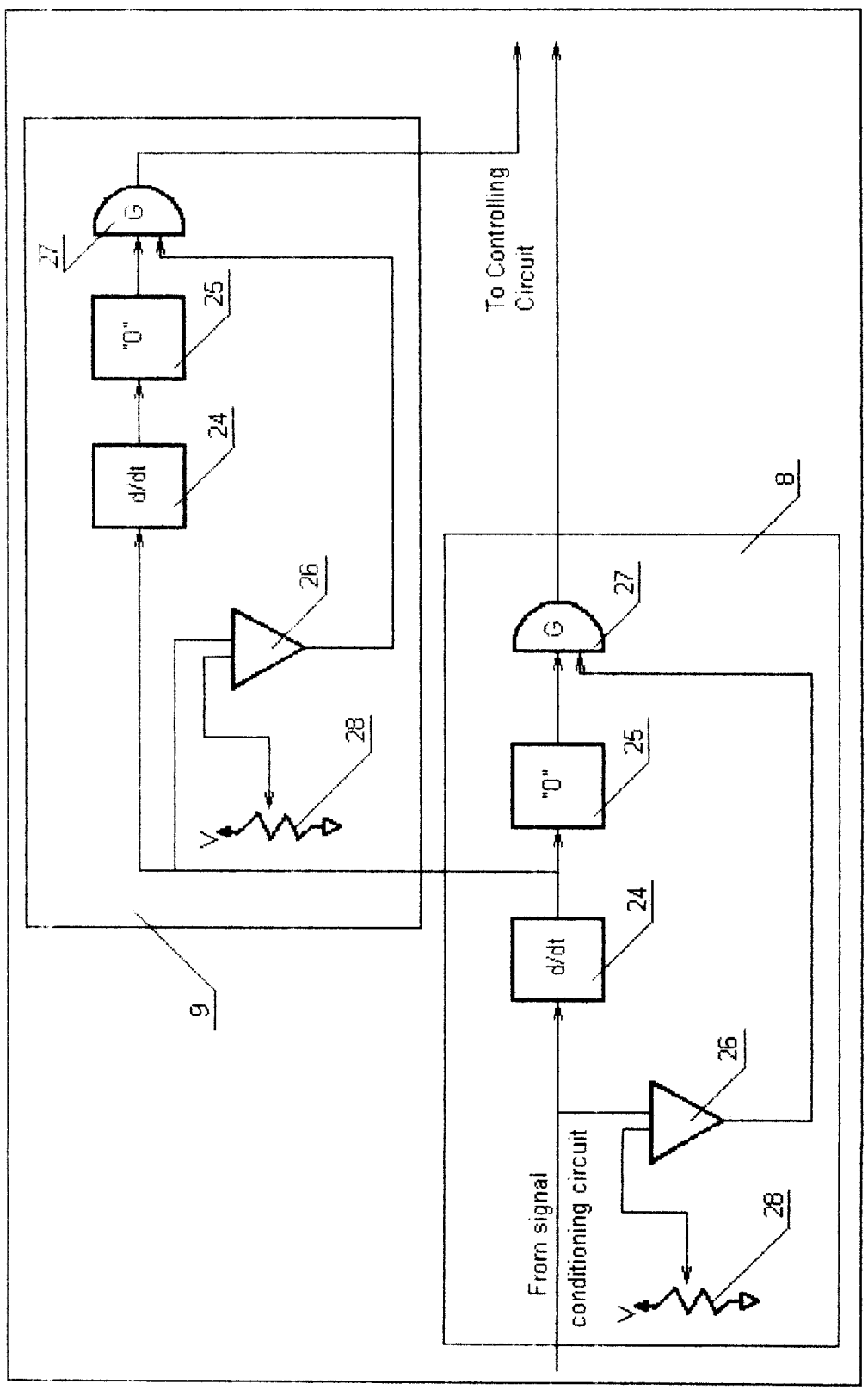
FIG. 17 is a detailed block diagram of a processing circuit.

Second peak detector 9 comprises the same blocks as peak detector 8 with the same function and is connected to the output of the differentiator 24. This peak detector produces a train of square pulse signals with leading edges corresponding to points of maximum rate of the systolic upstroke M in pulse waves. Corresponding waveform diagrams are illustrated in FIG. 16. FIG. 17 is a block diagram of entire processing circuit 2.

Figure 9:
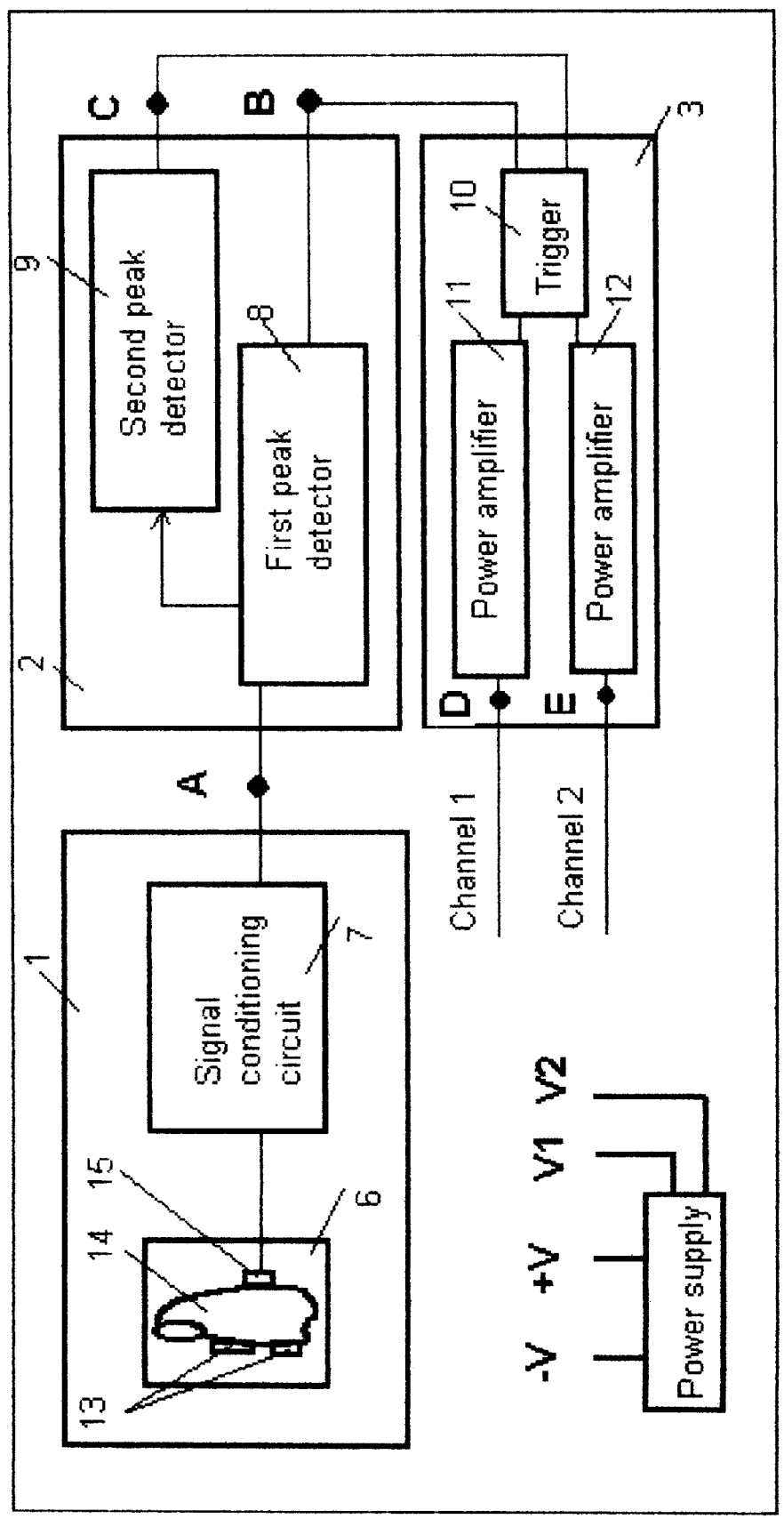
FIG. 9 is a block diagram of a biofeedback apparatus according to the present invention.
Figure 18:
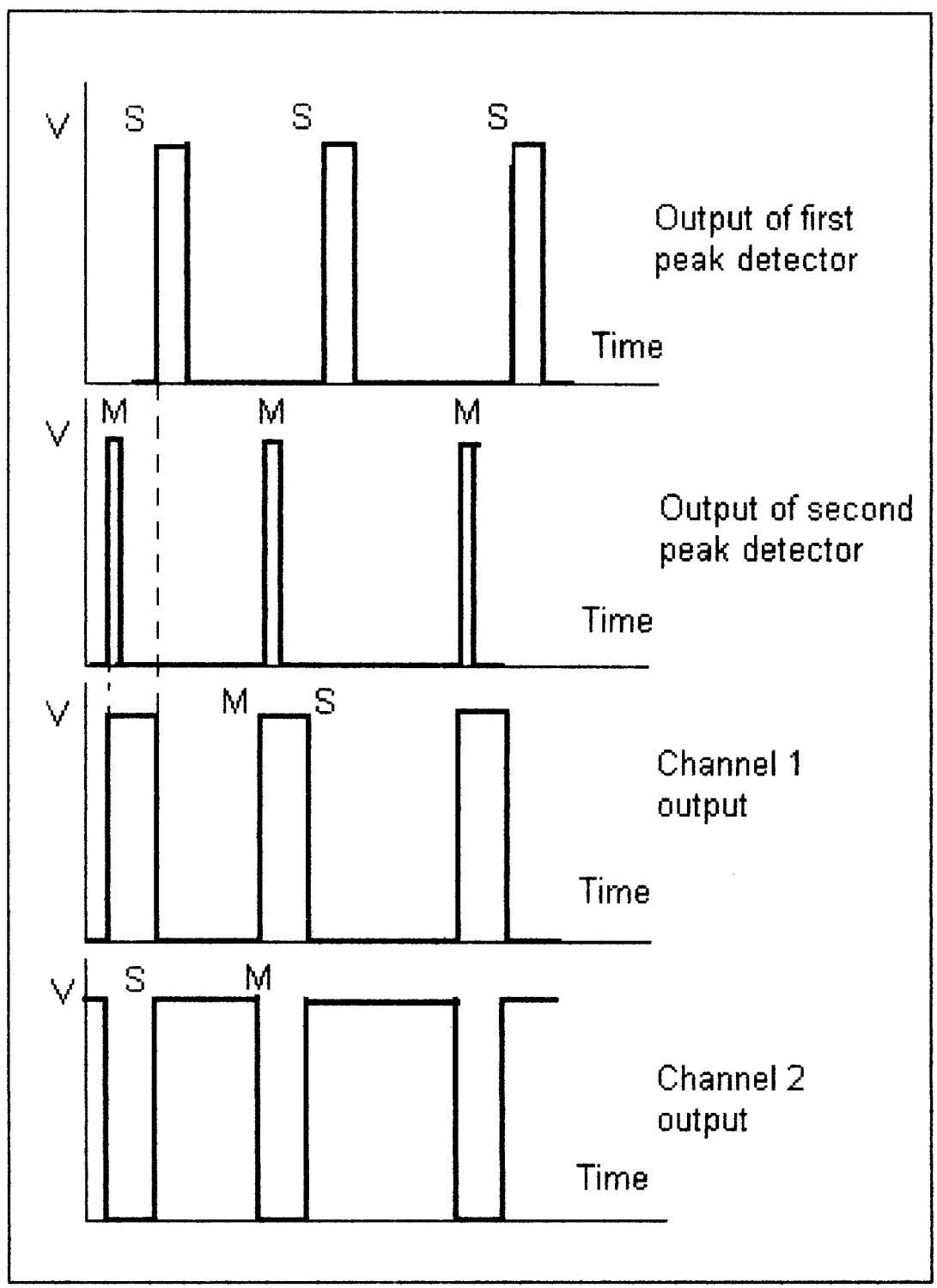
FIG. 18 illustrates waveform diagrams explaining signal convertion by a trigger.

The outputs of first and second peak detectors 8 and 9 are next inputted to a controlling circuit 3 which can be simply a trigger 10 (see FIG. 9). The trigger 10 provides to the outputs feedback square pulse signals synchronously and with duration to time intervals between points M and S in channel 1 and in channel 2 synchronously and with duration to time intervals between points S and M. FIG. 18 illustrates corresponding waveform translations.

After power amplification by amplifiers 11 and 12 the signals from channel 1 or 2 alternately turn a source of physical factor 4 "On" and "Off". It is assumed that the output of the source of physical factor is proportional to the intensity of control signal (if the signal is zero than the factor is "Off", if the signal is not zero than the factor is "On") In particular case of factor, which cannot be turned "Off" and "On" by controlling signals the appropriate modulator is used to the same effect.

Figure 19:
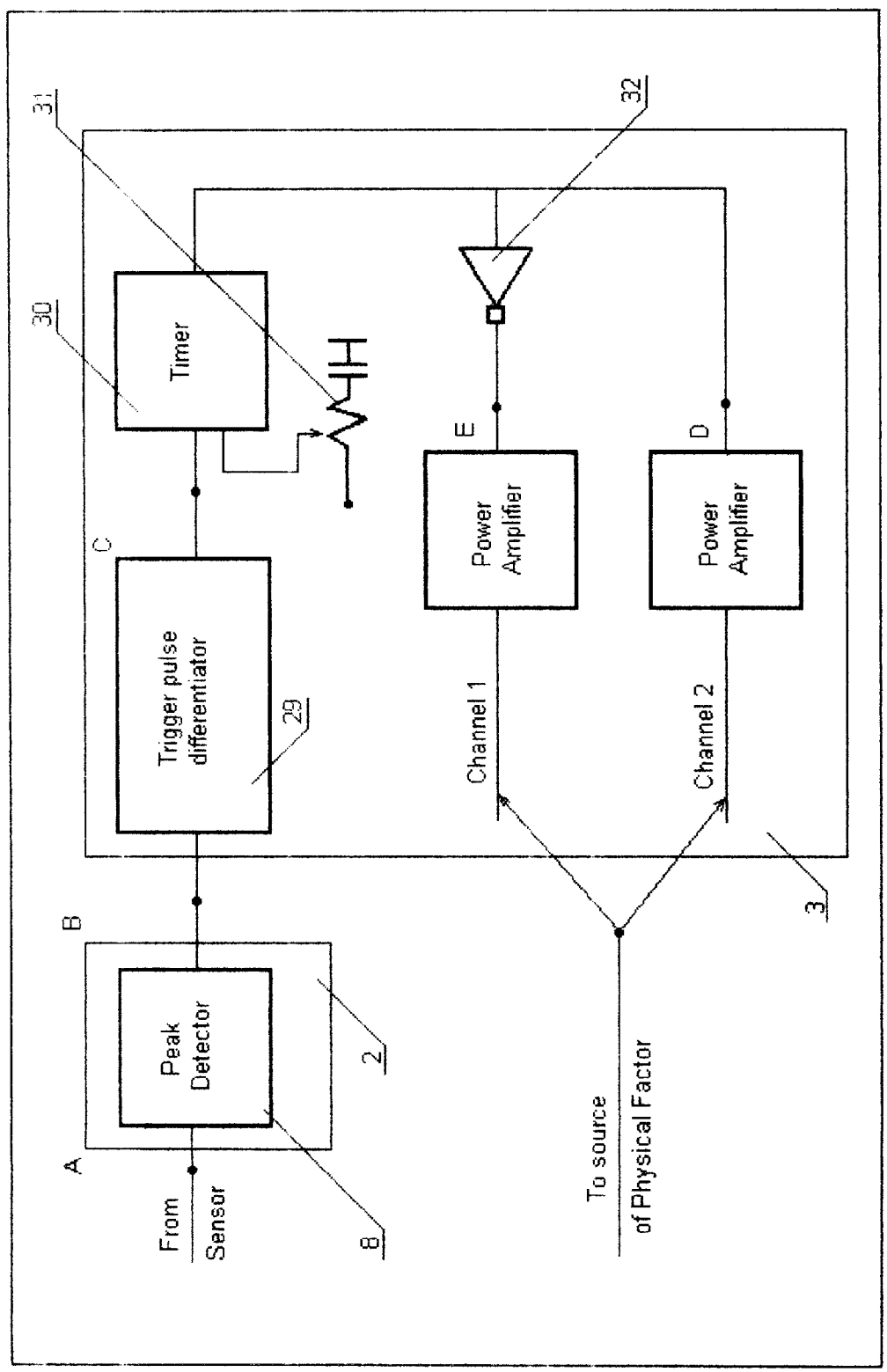
FIG. 19 is a block diagram of processing and controlling circuits according to the other embodiment of the invention.
Figure 20:
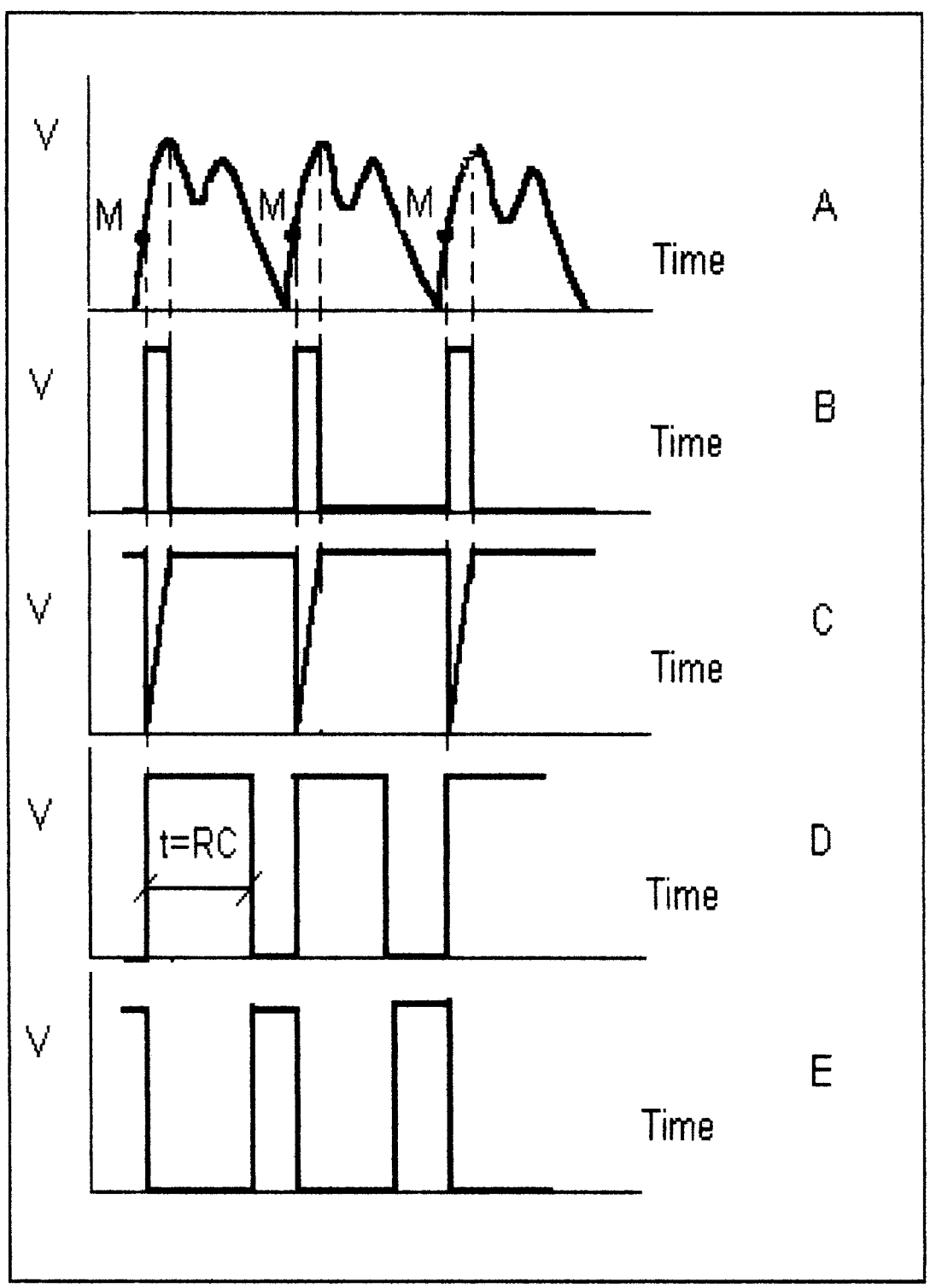
FIG. 20 is an illustration of waveform explaining signal translation by the circuit shown in FIG. 19.

Another embodiment of the present invention is based on empirical fact that the ratio of the systolic upstroke time to diastolic descent time has small changes from subject to subject which fall in a very narrow region from 1/7 to 1/5. FIG. 19 is a block diagram of processing and controlling circuits 2 and 3 according to this embodiment of the invention. The signal processing 2 comprises only one S-peak detector 8 connected to the output of sensor 1 and provides to the output a train of square pulse signals with interval being equal to the time interval between pulse waves. The outputted signals next are fed to a feedback controlling circuit. More specifically, the train of square pulse signals is fed to the input of a trigger pulse differentiator 29, which decrease the effective width of the pulses outputted by peak detector 8. Formed by the trigger pulse differentiator 29, pulse signals are fed to the input of a timer 30 which can be a commercial timer NE555. Timer provides the output of a train of square pulse signals synchronously to inputted pulse signals and with a preset by resistor 31 pulse width. An alternative output formed by inverter 32 outputs a train of opposite square pulse signals. FIG. 20 illustrates the signal translation by a circuit represented by block diagram 17.

Figure 21:
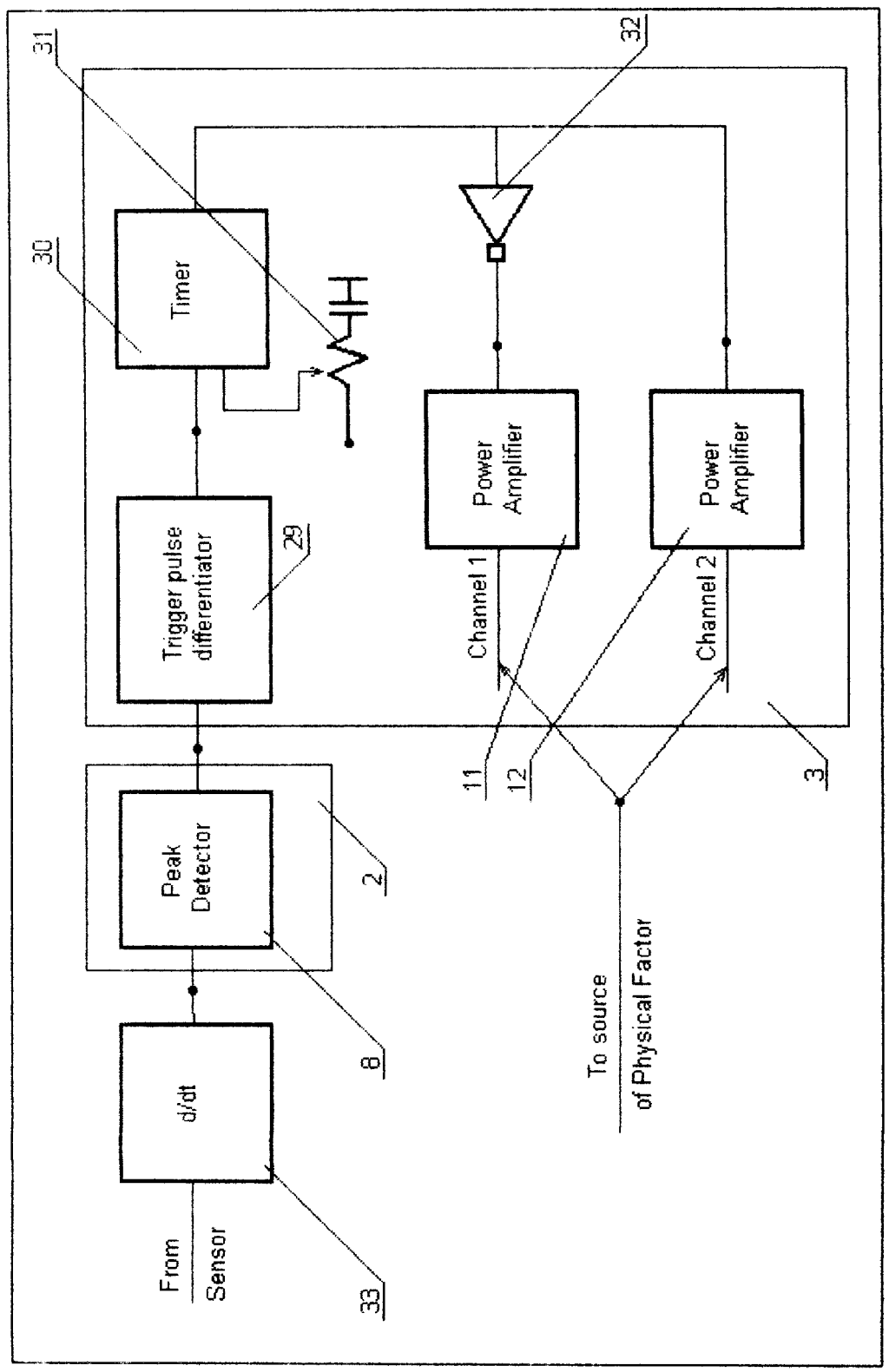
FIG. 21 is a block diagram of processing and controlling circuits corresponding to another embodiment of the present invention.

The other type of this embodiment of the present invention utilizes locating the pulse wave interval as a time interval between M-points in neighboring pulse waves. The block diagram of processing and controlling circuits 2 and 3 of this type is shown in FIG. 21. By comparing with FIG. 19 it is easy to see that the only difference of these circuits is that the pulse wave signals from sensor 1 are fed to an additional differentiator 33 which is similar to above described differentiator 24 and provides an output a differentiation wave. All other blocks in this type of embodiment are the same as shown in FIG. 19. In utilizing this embodiment of the present invention on a subject, initially an average pulse rate N is derived by one of conventional methods (even manually) and an average pulse wave interval T is calculated as given:

$$T = 60/N$$

Then by dividing the result of calculation in a proportion from range 1/7:1/5 the values for presetting the pulses' width are determined and set. For example, if the average pulse rate is 60, the average pulse wave interval will be 1 sec, and the pulse widths for ratio 1/5 will be correspondingly 200 and 800 ms.

Figure 22:
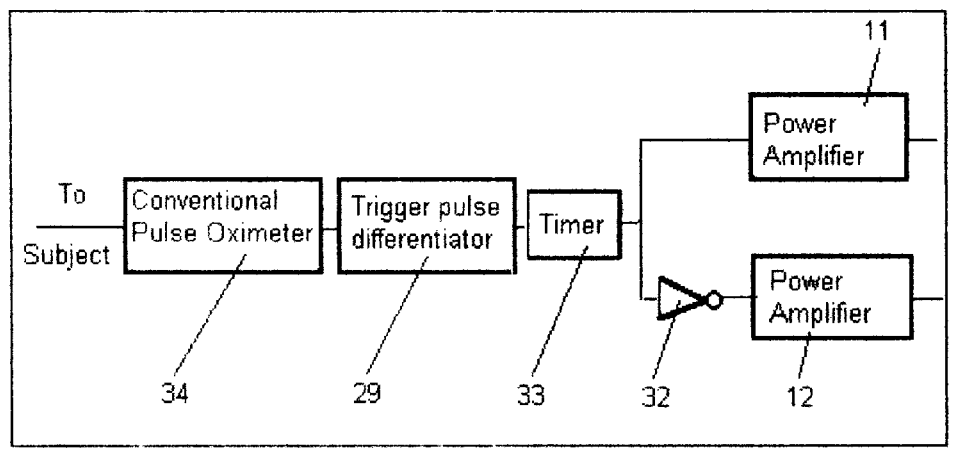
FIG. 22 is a block diagram of utilization of conventional pulse oxymeters in the present invention.

Further embodiment of the present invention is based on locating the systolic onset and peak points. This embodiment employs a conventional pulse oxymeter available for example from Ohmeda, Inc. as a source of signals corresponding to these points. Block diagram of the apparatus regarding this embodiment is shown in FIG. 22.

The present invention provides a unique method and apparatus for improvement of current treatments, which use of different physical factors.

Figure 25:
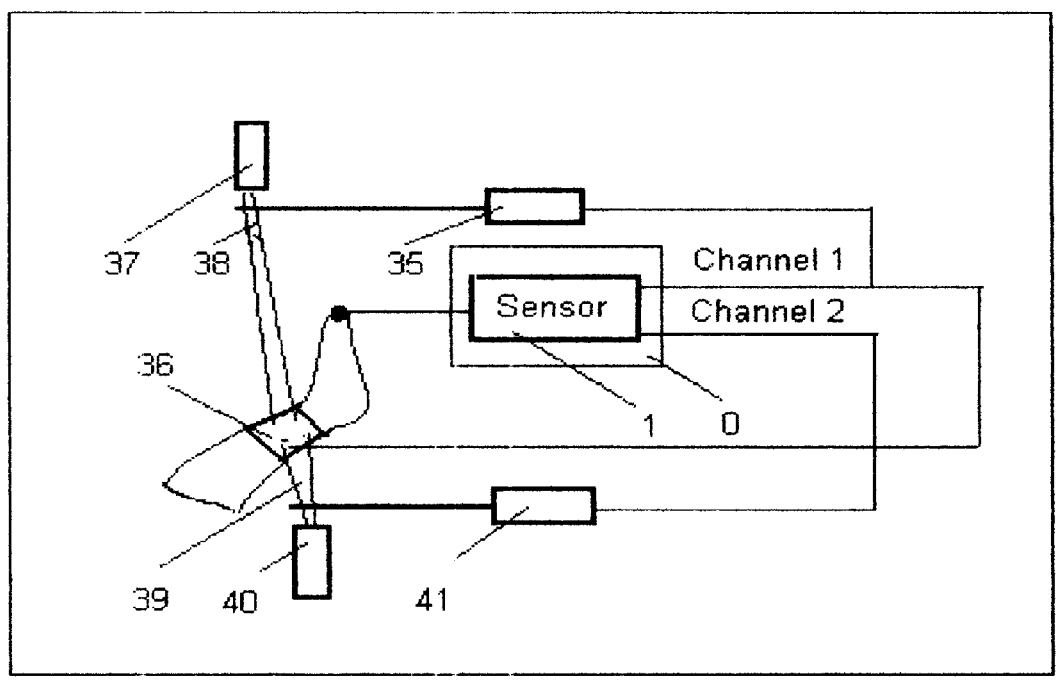
FIG. 25 is a block diagram illustrating another utilization of the present invention in radiotherapy combined with laser irradiation.
Figure 23:
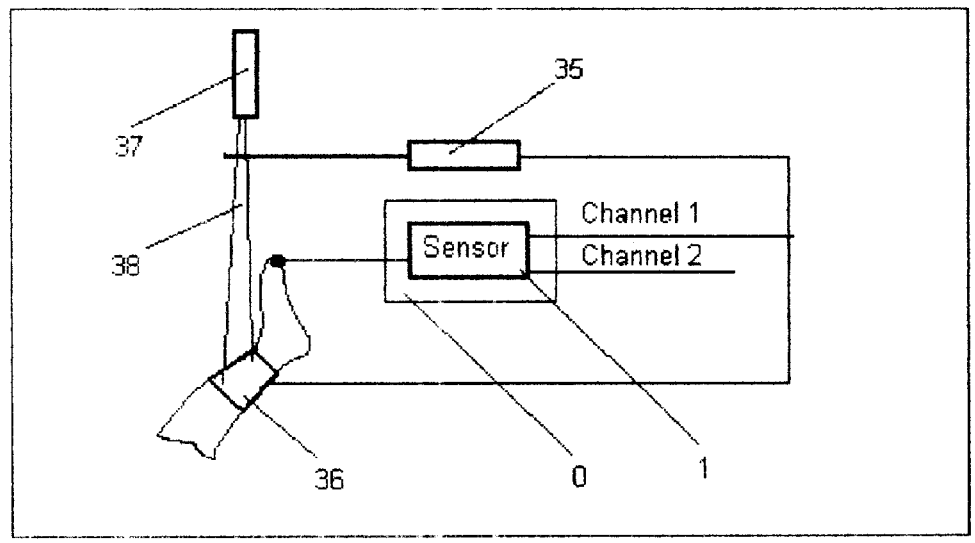
FIG. 23 is a block diagram illustrating utilization of the present invention in radiotherapy.
Figure 24:
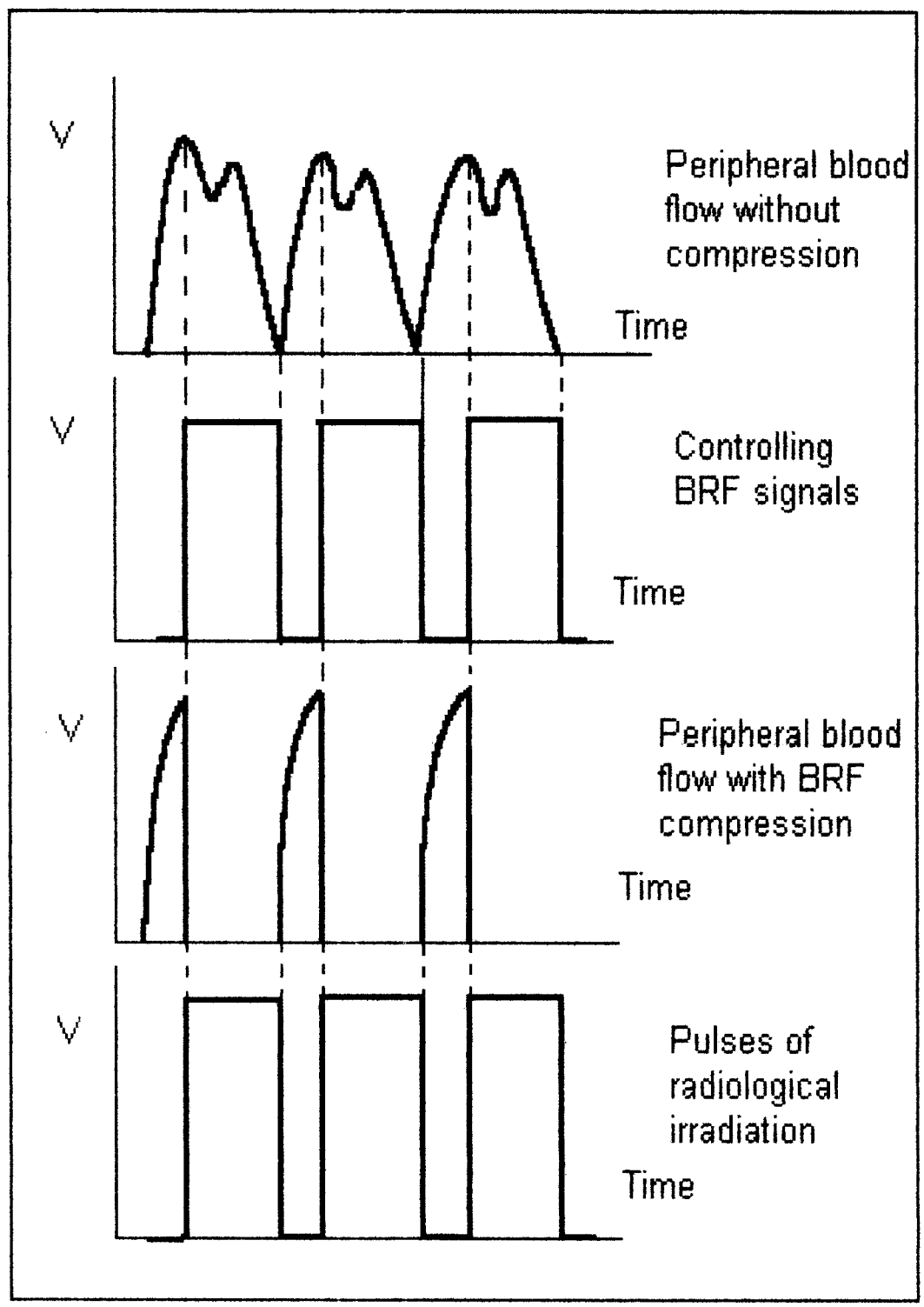
FIG. 24 illustrates the waveforms of the signals useful for explaining of the utilization of the present invention in radiotherapy.

Pertinent utilization of the present invention is improvement of treatment of human tumors by radiotherapy alone or combined with adjuvant such as tissue compression or laser irradiation. As it is, blood flow in the tissue, including tumors, markedly influences the tissue damage by radiation because it supplies oxygen, the most potent modifier of radiation effect and limits the dose of irradiation. This fact clearly indicate that blood evacuation by squeezing the tissue synchronously to the diastolic times of blood flow and synchronization to this intervals the irradiation by means of the present invention is a cardinal improvement of radiotherapeutic technologies. FIG. 23 illustrates utilizing the present invention for combined radiological irradiation and tissue compression. The targeted area located, for example on a leg of a subject, is irradiated by a beam 38 controlled by a shutter 35. This area is also compressed by a tissue compressing device 36, and a sensor 1 of bioresonance feedback apparatus 0 of this invention is positioned on a toe of the subject. The shutter 35 and tissue compression device 36 are both connected to the same output of apparatus 0. Controlled by apparatus 0 the tissue compression device 36 squeezes tissue and evacuate blood of the tissue synchronously to diastolic times of blood flow. Being synchronous to the same periods of time a radiological beam irradiates bloodless tissue, including tumor. Instead, during systolic periods either blood or tissue is not irradiated. Corresponding signals and time diagrams are shown in FIG. 24. FIG. 25 shows a block diagram of utilization the present invention for radiotherapy combined with tissue squeezing and laser irradiation. An additional laser beam 39 is interrupted by a shutter 41 controlled by the systolic output of the apparatus 0.

It will be understood that each of the elements described above, or two or more together, may also find a useful application in other types of constructions differing from the types described above.

While the invention has been illustrated and described as embodied in bioresonance feedback method and apparatus, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A bioresonance feedback method, comprising the steps of applying a physical factor to a subject for medical purposes; and automatically coordinating the applying of the physical factor to the subject with cycles of arterial blood pulse flow of the subject.

2. A biofeedback method as defined in claim 1, wherein said coordinating includes sensing arterial blood pulse waves of a subject's body, selecting in each pulse wave a systolic influx and diastolic drain blood cycles, generating feedback signals in a first channel synchronously to the systolic influx cycles and in a second channel synchronously to diastolic drain cycles, and synchronizing the physical action to said cycles by controlling the physical action by feedback signals of the first and second channels.

3. A biofeedback method as defined in claim 2, wherein said sensing includes sensing the pulse waves by photoplethysmography.

4. An biofeedback apparatus comprising means for application of a physical action to a subject for medical purposes; and means for automatically coordinating the applying the physical action to the subject, in accordance with cycles of arterial blood pulse flow of the subject.

5. A biofeedback method for applying a physical action to a subject for medical purposes comprising the steps of coordinating applying of a physical factor to a subject with cycles of arterial blood pulse flow of the subject, said coordinating including sensing arterial blood pulse waves of a subject's body, selecting in each pulse wave a systolic influx and diastolic drain blood cycles, generating feedback signals in a first channel synchronously to the systolic influx cycles and in a second channel synchronously to a diastolic drain cycles, and synchronizing the physical action to said cycles by controlling the physical action by feedback signals of the first and second channels, said sensing including photo-electrically detecting the pulse waves from a nearest to an effected area location where a pulse wave can be detected.

6. A biofeedback method for applying a physical action to a subject for medical purposes comprising the steps of coordinating applying of a physical action to a subject with cycles of arterial blood pulse flow of the subject, said coording including sensing arterial blood pulse waves of a subject's body, selecting in each pulse wave a systolic influx and diastolic drain blood cycles, generating feedback signals in a first channel synchronously to the systolic influx cycles and in a second channel synchronously to a diastolic drain cycles, and synchronizing the physical action to said cycles by controlling the physical action by feedback signals of the first and second channels, said selecting including locating in the pulse wave points of discrimination between said systolic upstroke and diastolic descent intervals.

7. A biofeedback method as defined in claim 6, wherein said locating the points of discrimination includes locating systolic peak points and points of maximum systolic upstroke rate.

8. A biofeedback method as defined in claim 6, wherein locating the points of discrimination includes locating a points of discrimination of systolic onset and systolic peak points.

9. A biofeedback method as defined in claim 6, wherein said locating the points of discrimination includes dividing an average time interval between pulse waves in a predetermined proportion.

10. A biofeedback method as defined in claim 9, wherein said dividing includes dividing a time interval between points of maximum systolic upstroke rate.

11. A biofeedback method as defined in claim 9, wherein said dividing includes dividing an interval between said systolic peak points.

12. A biofeedback method as defined in claim 9, wherein said dividing includes dividing in the predetermined proportion within a range from 1/7 to 1/5.

13. A biofeedback method as defined in claim 7, wherein said locating the points of maximum systolic upstream rate and systolic peak points includes differentiating twice the pulse wave with respect to time to produce first and second differentiated waves, comparing amplitudes of the pulse wave and the first differentiating wave with predetermined reference signals for discriminating the systolic peaks on the pulse wave and positive peaks in the first differentiated wave, detecting zero-crossing of the first and second differentiated waves, and locating the systolic peak points as points of the first differentiated wave zero-crossing within discriminated systolic peak and locating the points of maximum systolic upstroke rate as points of the second differentiated wave zero-crossing with discriminated positive peak of the first differentiated wave.

14. A biofeedback method as defined in claim 6, wherein said generating includes providing square pulse signals in the first channel synchronously and with a pulse width being equal to occurrence and duration of the systolic upstroke intervals and in the second channels synchronously and with a pulse width being equal to occurrence and duration of the diastolic decent intervals.

15. An apparatus for application of a physical action to a subject for medical purposes, comprising means for applying the physical action to a subject in accordance with cycles of arterial blood pulse flow of the subject, said applying means including a sensor for sensing blood pulses from a body of the subject comprising a probe with a source and a detector of electromagnetic radiation mounted with possibility for gripping a part of the body at a place where a portion of an electromangetic radiation attenuated by blood content tissue is detachable, sensing means for producing an output signal corresponding to an alternative component of the attenuated electromagnetic radiation, a conditioning electronic circuit to which said probe is electrically connected, input conditioning means connected to said detector for removing a direct current component from a pulse wave signal and for smoothing an alternative component wave form, a processing electronic circuit to which said conditioning circuit electrically connected, input processing means connected to said signal conditioning circuit for locating on the pulse wave points of discrimination between systolic upstroke and diastolic descent intervals, locating means identifying time moments corresponding to the points on the pulse wave, a feedback controlling electronic circuit to which said processing circuit is electrically connected, input controlling means connected to said processing circuit for providing to first output channel square electrical pulses synchronously and with duration equal to occurrence and duration of systolic upstroke intervals and providing to a second output channel square electrical pulses synchronously and with duration equal to occurrence and duration of diastolic descent intervals, and a source of electrical energy to which said electronic circuits are electronically connected.

16. An apparatus as defined in claim 15, wherein said source and said detector of electromagnetic radiation are light emitting diode and photodiode.

17. An apparatus as defined in claim 15, wherein said conditioning circuit includes a first differential amplifier with a negative terminal to which said photodiode is electrically connected, a second differential amplifier with a negative terminal to which said photodiode is electrically connected, an inverter-filter to which said second differential amplifier is electrically connected and whose output is electrically connected through a resistor to said negative terminal of said first differential amplifier, and a filter to which an output of said first differential amplifier is electrically connected for eliminating noise and ambient-like signal.

18. An apparatus as defined in claim 15, wherein said processing circuit includes a first peak detector to which said sensing circuit is electrically connected for detecting systolic upstroke peak points on the pulse wave, and a second peak detector to which said sensing circuit is also electrically connected for detecting points of maximal systolic upstroke rate on the pulse wave.

19. An apparatus as defined in claim 18, wherein said feedback controlling circuit includes a trigger to which said first peak detector and said second peak detector are electrically connected, input triggering means for providing to said first output channel square electric pulses sychronously and with duration equal to occurrence and duration of the systolic upstroke intervals and providing to said second output channel square electric pulses synchronously and with duration equal to occurrence and duration of the diastolic decent intervals, and first and second power amplifier to which correspondingly are connected said first and second channels for power amplifying of the square electric pulses.

20. An apparatus as defined in claim 15, wherein said processing circuit includes a first comparator to which said conditioning circuit and first source of reference signal are electrically connected, input comparing means for providing to the output square pulses corresponding to time intervals when amplitudes of the pulse waves of the alternative component are above a predetermined value of a first reference signal, a first differentiating circuit to which said conditioning circuit is electrically connected, input differentiating means for providing to the output a first differentiated wave, a first zero-cross detector to which said first differentiating circuit is electrically connected for detecting zero-crossing points of said first differentiated wave, a first logic gate to which said first zero-cross detector and said first comparator are electrically connected for selecting peak systolic points, a second comparator to which said first differentiating circuit and a second source of reference signal are electrically connected, input comparing means for providing to the output square pulses corresponding to time intervals which amplitudes of positive half wave of said first differentiated wave are above a predetermined value of the second reference signal, a second differentiating signal to which said first differenting circuit is electrically connected, input differentiating means for providing to the output a second differentiated wave, a second zero-cross detector to which said second differentiating circuit is electrically connected for detecting zero-crossing points of said second differentiated wave, and a second logic gate to which said second zero-cross detector and said second comparator are electrically connected for selecting points of maximal systolic upstroke rate.

21. An apparatus as defined in claim 20, wherein said first and second logic gates are an AND gate.

22. An apparatus as defined in claim 20, wherein said filter is a low pass filter.

23. An apparatus as defined in claim 15, wherein said processing circuit includes only a systolic peak detector which is electrically connected to said sensor for producing a train of square pulse signals synchronously to systolic peak points.

24. An apparatus as defined in claim 23, wherein said controlling circuit includes a trigger pulse differentiator to which said peak detector is electrically connected for decreasing a pulse width, a timer to which said trigger pulse differentiator is electrically connected for providing to the output square pulse signals with pulse width which is equal to a predetermined portion of a time between pulse waves, and an invertor to which said timer is electrically connected for establishing a second output for pulse signals having pulse width equal to a difference between time between pulse waves and a pulse width of signals in said first channel.

25. An apparatus as defined in claim 24, wherein a predetermined quotient is within a range from 1/7 to 1/5.

26. An apparatus as defined in claim 24, wherein said points of discrimination between the pulse waves are points of maximal systolic upstroke rate.

27. An apparatus as defined in claim 24, wherein points of discrimination between the pulse waves are systolic peak points.

28. An apparatus as defined in claim 15, wherein said sensor and said processing circuit are a pulse oxymeter.

* * * * *